US010421816B2

(12) United States Patent
Adams et al.

(10) Patent No.: US 10,421,816 B2
(45) Date of Patent: *Sep. 24, 2019

(54) MULTIVALENT ANTIBODIES

(71) Applicant: UCB PHARMA S.A., Brussels (BE)

(72) Inventors: Ralph Adams, Slough (GB); Emma Dave, Slough (GB); David Paul Humphreys, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/165,131

(22) Filed: May 26, 2016

(65) Prior Publication Data

US 2016/0333105 A1    Nov. 17, 2016

Related U.S. Application Data

(63) Continuation of application No. 13/395,235, filed as application No. PCT/GB2010/001711 on Sep. 10, 2010, now abandoned.

(60) Provisional application No. 61/241,159, filed on Sep. 10, 2009.

(51) Int. Cl.
| | |
|---|---|
| *C07K 16/46* | (2006.01) |
| *C07K 16/28* | (2006.01) |
| *C07K 7/06* | (2006.01) |
| *C07K 7/08* | (2006.01) |
| *C07K 16/18* | (2006.01) |

(52) U.S. Cl.
CPC ............ *C07K 16/2878* (2013.01); *C07K 7/06* (2013.01); *C07K 7/08* (2013.01); *C07K 16/18* (2013.01); *C07K 16/2875* (2013.01); *C07K 16/468* (2013.01); *C07K 2317/24* (2013.01); *C07K 2317/31* (2013.01); *C07K 2317/522* (2013.01); *C07K 2317/53* (2013.01); *C07K 2317/55* (2013.01); *C07K 2317/565* (2013.01); *C07K 2317/624* (2013.01); *C07K 2317/92* (2013.01)

(58) Field of Classification Search
CPC .............. C07K 16/468; C07K 2317/31; C07K 2317/50–55; C07K 2317/60; C07K 2317/64; C07K 2317/66
See application file for complete search history.

(56) References Cited

U.S. PATENT DOCUMENTS

| | | | |
|---|---|---|---|
| 5,747,654 A | 5/1998 | Pastan et al. | |
| 5,972,901 A | 10/1999 | Ferkol et al. | |
| 5,989,830 A | 11/1999 | Davis et al. | |
| 7,150,872 B2 | 12/2006 | Whitlow et al. | |
| 7,829,084 B2 | 11/2010 | Ledbetter et al. | |
| 8,629,246 B2 | 1/2014 | Humphreys et al. | |
| 9,040,048 B2 * | 5/2015 | Adams ............... | C07K 16/2866 424/136.1 |
| 9,309,327 B2 * | 4/2016 | Humphreys ........... | C07K 16/00 |
| 9,828,438 B2 * | 11/2017 | Humphreys ........... | C07K 16/00 |
| 9,873,735 B2 * | 1/2018 | Adams ............... | C07K 16/2866 |
| 2005/0084906 A1 | 4/2005 | Goetsch et al. | |
| 2006/0147445 A1 | 7/2006 | O'Keefe et al. | |
| 2009/0155275 A1 | 6/2009 | Wu et al. | |
| 2010/0215664 A1 | 8/2010 | Kolkman et al. | |
| 2010/0239582 A1 | 9/2010 | Humphreys et al. | |
| 2011/0033483 A1 | 2/2011 | Thompson et al. | |
| 2011/0184152 A1 | 7/2011 | Adams et al. | |
| 2012/0316324 A1 | 12/2012 | Adams et al. | |
| 2013/0053549 A1 | 2/2013 | Adams et al. | |
| 2013/0066054 A1 | 3/2013 | Humphreys et al. | |
| 2016/0031974 A1 * | 2/2016 | Adams ............... | C07K 16/2866 424/136.1 |
| 2016/0244532 A2 * | 8/2016 | Heywood ............ | C08G 59/066 |
| 2016/0311930 A1 * | 10/2016 | Humphreys ........... | C07K 16/00 |

FOREIGN PATENT DOCUMENTS

| | | | |
|---|---|---|---|
| WO | WO199837200 | 8/1998 | |
| WO | WO9964460 | 12/1999 | |
| WO | WO-0177342 A1 * | 10/2001 | ............. C07K 16/00 |
| WO | WO2004081026 | 9/2004 | |
| WO | WO2005003170 | 1/2005 | |
| WO | WO2006034488 | 3/2006 | |
| WO | WO2007010231 | 1/2007 | |

(Continued)

OTHER PUBLICATIONS

Paul, Fundamental Immunology, 3rd Edition, 292-295 (1993).

(Continued)

*Primary Examiner* — Jessica H Roark
(74) *Attorney, Agent, or Firm* — McDonnell Boehnen Hulbert & Berghoff LLP

(57) ABSTRACT

The present invention provides a multivalent antibody or a heavy/light chain component thereof comprising: a heavy chain comprising a constant region fragment, said constant region fragment located between two variable domains which are not a cognate pair, the heavy chain further comprising an Fc region with at least one domain selected from CH2, CH3 and combinations thereof, with the proviso that the heavy chain contains no more than one CH1 domain and only contains two variable domains, and a light chain comprising a constant region fragment located between two variable domains which are not a cognate pair, wherein said heavy and light chains are aligned to provide a first binding site formed by a first cognate pair of variable domains and a second binding site formed by a second cognate pair of variable domains.

9 Claims, 10 Drawing Sheets

Specification includes a Sequence Listing.

(56) References Cited

FOREIGN PATENT DOCUMENTS

| WO | WO2008038024 | 4/2008 | | |
|---|---|---|---|---|
| WO | WO2009018386 | 2/2009 | | |
| WO | WO-2009040562 A1 | * | 4/2009 | ............ C07K 16/00 |
| WO | WO2009018386 | 5/2009 | | |
| WO | WO2010035012 | 4/2010 | | |

OTHER PUBLICATIONS

Bending, Method: A Companion to Methods in Enzymology, 8:83-93 (1995).

Reiter, The Journal of Biological Chemistry, 269:18327-18331 (1994).

Chapman, Andrew P., "PEGylated antibodies and antibody fragments for improved therapy: A review", Advanced Drug Deliver Reviews, 54, 531-545 (2002).

Natarajan, et al., "Characterization of site-specific SCFV PEGylation tumor-targeting pharmaceuticals", Bioconjugate Chemistry, 16:113-121 (2005).

Melmed, Gil, et al., "Certolizumab pego", Nature Review Drug Discovery, 7:641-642 (2008).

Blick, et al., "Cetolizumab pegol: in Crohn's Disease", Biodrugs: Clinical Innunotherapeutics, Biopharmaceuticals and Gene Therapy, 21:195-201 (2007).

Ton, et al., "Phase I evaluation of CDP791, a PEGylated Di-Fab' conjugate that binds vascular endothelial growth factor receptor 2", Clinical Cancer Research: An Official journal of the American Association for Cancer Research, 13:7113-7118 (2007).

Chan, et al., "Therapeutic antibodies for autoimmunity and inflammation", Nature Reviews, 10:301-316 (2010).

Miller, et al., "Design, Construction and in Vitro Analyses of Multivalent Antibodies", The Journal of Immunology, 170:4854-4861 (2003).

Wu, et al., "Simultaneous targeting of multiple disease mediators by a dual-variable-domain immunoglobulin", Nature Biotechnology, 25:1290-1297 (2007).

Abbott Scientists Create One Molecule with Two Antibody Functions: Retrieved from Internet on Oct. 17, 2013; http://www.drugs.com/clinical_trials/abbott-scientists-create-one-molecule-two-antibody-functions-2311.html.

Alamagro & Fransson, Frontiers in Bioscience, 13:1619-33 (2008).

De Genst, et al., Dev Comp. Immunol, 30:187-98 (2006).

George & Huston, "Bispecific Antibody Engineering" in the Antibodies, Chapter 6, 4:99-141 (1997).

Hudson & Kortt, J. Immunol Methods, 231:177-89 (1999).

Webber, et al., Mol. Immunol., 32:249-58 (1995).

* cited by examiner

Variable domain first cognate pair

Heavy chain constant regions

CL

Variable domain of second cognate pair

Peptide linker

Disulfide bond

Figure 3B
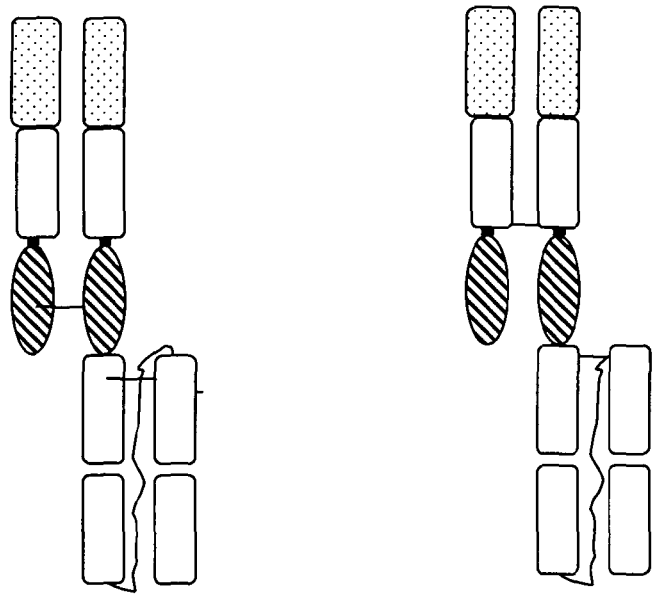
E  F
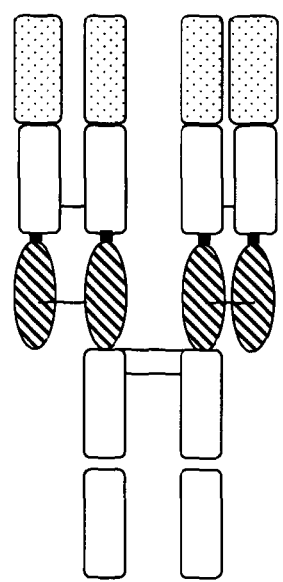  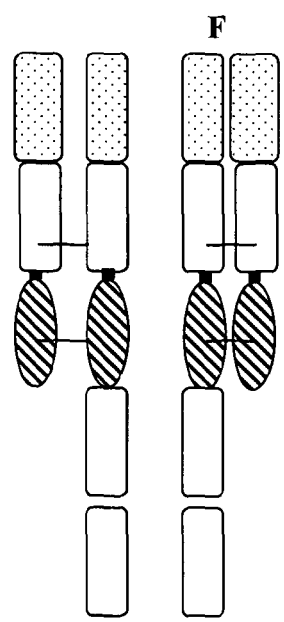
G  H

Figure 4
Heavy chain (SEQ ID NO:66)
Coding sequence of (A26 gH2 gamma 1-CH1 2G4S 645 gH1)$_2$ gamma 1 Fc

```
gaggtgcagctggtcgagtctggaggcgggcttgtccagcctggagggagcctgcgtctctc
ttgtgcagcaagcggtttcacgttcaccaactacggtatccactggattcgtcaggcaccag
gtaaaggtctggaatgggtagcctctatctctccgtctggtggtctgacgtactaccgtgac
tctgtcaaaggtcgtttcaccatctctcgtgatgacgcgaaaaactctccgtacctgcagat
gaactctctgcgtgcagaagataccgcagtgtactactgcgctactggtggtgaaggtatct
tcgactactggggtcagggtaccctggtaactgtctcgagcgcttctaccaaaggtccgagc
gttttcccactggctccgagctctaaatccacctctggtggtacggctgcactgggttgcct
ggtgaaagactacttcccagaaccagttaccgtgtcttggaactctggtgcactgacctctg
gtgttcacacctttccagcagttctgcagtcttctggtctgtactccctgtctagcgtggtt
accgttccgtcttcttctctgggtactcagacctacatctgcaacgtcaaccacaaaccgtc
caacacgaaagtggacaaaaaagtcgagccgaaatcctgttccggaggtggcggttctggtg
gcggtggatccgaggttcagctgctggagtctggaggcgggcttgtccagcctggagggagc
ctgcgtctctcttgtgcagtaagcggcatcgacctgtccaactacgcgattaactgggtacg
tcaggcaccgggtaaaggtctggaatggatcggcatcatctgggcctctggtacgaccttct
acgctacttgggccaaaggtcgtttcaccatctcccgtgactctaccaccgtgtacctgcag
atgaactctctgcgtgcggaagacactgcggtttactattgcgcgcgtaccgttccgggcta
ttctactgcaccgtacttcgacctgtggggtcagggtactctggttaccgtctcgtctgaca
aaactcacacatgccaccgtgcccaggtaagccagcccaggcctcgccctccagctcaagg
cgggacaggtgccctagagtagcctgcatccagggacaggccccagccgggtgctgacacgt
ccacctccatctcttcctcagcacctgaactcctgggggaccgtcagtcttcctcttcccc
ccaaaacccaaggacaccctcatgatctcccggacccctgaggtcacatgcgtggtggtgga
cgtgagccacgaagaccctgaggtcaagttcaactggtacgtggacggcgtggaggtgcata
atgccaagacaaagccgcgggaggagcagtacaacagcacgtaccgtgtggtcagcgtcctc
accgtcctgcaccaggactggctgaatggcaaggagtacaagtgcaaggtctccaacaaagc
cctcccagcccccatcgagaaaaccatctccaaagccaaaggtgggacccgtggggtgcgag
ggccacatggacagaggccggctcggcccaccctctgccctgagagtgaccgctgtaccaac
ctctgtccctacagggcagccccgagaaccacaggtgtacaccctgccccatcccgggatg
agctgaccaagaaccaggtcagcctgacctgcctggtcaaaggcttctatcccagcgacatc
gccgtggagtgggagagcaatggcagccggagaacaactacaagaccacgcctcccgtgct
ggactccgacggctccttcttcctctacagcaagctcaccgtggacaagagcaggtggcagc
aggggaacgtcttctcatgctccgtgatgcatgaggctctgcacaaccactacacgcagaag
agcctctccctgtctccgggtaaatgagtgcgacggccggcaagccccgctccccgggctc
tcgcggtcgcacgaggatgcttggcacgtacccctgtacatacttcccgggcgcccagcat
ggaaataaagcacccagcgctgccctgggccgagctcgaattc
```

The above sequence is composed of the following:

A26 gH2
```
Gaggtgcagctggtcgagtctggaggcgggcttgtccagcctggagggagcctgcgtctctc
ttgtgcagcaagcggtttcacgttcaccaactacggtatccactggattcgtcaggcaccag
gtaaaggtctggaatgggtagcctctatctctccgtctggtggtctgacgtactaccgtgac
tctgtcaaaggtcgtttcaccatctctcgtgatgacgcgaaaaactctccgtacctgcagat
gaactctctgcgtgcagaagataccgcagtgtactactgcgctactggtggtgaaggtatct
tcgactactggggtcagggtaccctggtaactgtctcgagc (SEQ ID NO:67)
```
EVQLVESGGGLVQPGGSLRLSCAASGFTFTNYGIHWIRQAPGKGLEWVASISPSGGLTYYRD
SVKGRFTISRDDAKNSPYLQMNSLRAEDTAVYYCATGGEGIFDYWGQGTLVTVSS(SEQ ID NO:68)

Figure 5

Gamma 1 CH1
Gcttctaccaaaggtccgagcgttttcccactggctccgagctctaaatccacctctggtgg
tacggctgcactgggttgcctggtgaaagactacttcccagaaccagttaccgtgtcttgga
actctggtgcactgacctctggtgttcacacctttccagcagttctgcagtcttctggtctg
tactccctgtctagcgtggttaccgttccgtcttcttctctgggtactcagacctacatctg
caacgtcaaccacaaaccgtccaacacgaaagtggacaaaaagtcgagccgaaatcctgt
(SEQ ID NO:69)
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSC (SEQ ID NO:70)

2(G4S)
tccggaggtggcggttctggtggcggtggatcc (SEQ ID NO:71)
SGGGGSGGGGS (SEQ ID NO:72)

645 gH1
Gaggttcagctgctggagtctggaggcgggcttgtccagcctggagggagcctgcgtctctc
ttgtgcagtaagcggcatcgacctgtccaactacgcgattaactgggtacgtcaggcaccgg
gtaaaggtctggaatggatcggcatcatctgggcctctggtacgaccttctacgctacttgg
gccaaaggtcgtttcaccatctcccgtgactctaccaccgtgtacctgcagatgaactctct
gcgtgcggaagacactgcggtttactattgcgcgcgtaccgttccgggctattctactgcac
cgtacttcgacctgtggggtcagggtactctggttaccgtctcgtct (SEQ ID NO:73)
EVQLLESGGGLVQPGGSLRLSCAVSGIDLSNYAINWVRQAPGKGLEWIGIIWASGTTFYATW
AKGRFTISRDSTTVYLQMNSLRAEDTAVYYCARTVPGYSTAPYFDLWGQGTLVTVSS (SEQ ID NO:74)

Gamma 1 Fc (composed of hinge, CH2 and CH3)
Gacaaaactcacacatgcccaccgtgcccaggtaagccagcccaggcctcgcctccagctc
aaggcgggacaggtgccctagagtagcctgcatccagggacaggccccagccgggtgctgac
acgtccacctccatctcttcctcagcacctgaactcctgggggaccgtcagtcttcctctt
cccccaaaacccaaggacaccctcatgatctcccggacccctgaggtcacatgcgtggtgg
tggacgtgagccacgaagaccctgaggtcaagttcaactggtacgtggacggcgtggaggtg
cataatgccaagacaaagccgcgggaggagcagtacaacagcacgtaccgtgtggtcagcgt
cctcaccgtcctgcaccaggactggctgaatggcaaggagtacaagtgcaaggtctccaaca
aagcccctccagcccccatcgagaaaaccatctccaaagccaaaggtgggacccgtggggtg
cgagggccacatggacagaggccggctcggcccaccctctgcctgagagtgaccgctgtac
caacctctgtcctacagggcagccccgagaaccacaggtgtacaccctgcccccatcccgg
gatgagctgaccaagaaccaggtcagcctgacctgcctggtcaaaggcttctatcccagcga
catcgccgtggagtgggagagcaatgggcagccggagaacaactacaagaccacgcctcccg
tgctggactccgacggctccttcttcctctacagcaagctcaccgtggacaagagcaggtgg
cagcaggggaacgtcttctcatgctccgtgatgcatgaggctctgcacaaccactacacgca
gaagagcctctccctgtctccgggtaaatga (SEQ ID NO:75)
DKTHTCPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPGK (SEQ ID NO:76)

Figure 6

Light chain

Coding sequence of A26 gL8 CK 2G4S 645 gL1 c-myc tag (SEQ ID NO:77)
gatatccagatgacccagagtccaagcagtctctccgccagcgtaggcgatcgtgtgacta
ttacctgtcgtgcaacccagagcatctacaacgctctggcttggtatcagcagaaaccggg
taaagcgccaaaactcctgatctacaacgcgaacactctgcataccggtgttccgtctcgt
ttctctgcgtctggttctggtacggactctactctgaccatctcctctctgcagccggaag
atttcgcgacctactactgccagcagtactacgattacccactgacgtttggtggtggtac
caaagttgagatcaaacgtacggttgcagctccatccgtcttcatctttccaccgtctgac
gaacagctcaaatctggtactgcttctgtcgtttgcctcctgaacaacttctatccgcgtg
aagcgaaagtccagtggaaagtcgacaacgcactccagtctggtaactctcaggaatctgt
gaccgaacaggactccaaagactccacctactctctgtctagcaccctgactctgtccaaa
gcagactacgagaaacacaaagtgtacgcttgcgaagttacccatcagggtctgagctctc
cggttaccaaaagctttaatagaggggagtgttccggaggcggtggctctggtggcggtgg
atccgatatcgtgatgacccagagtccaagcagtgtttccgccagcgtaggcgatcgtgtg
actattacctgtcagtcctctccgagcgtttggtccaacttcctgagctggtaccagcaga
aaccgggtaaagccccgaaactgctgatctacgaggcgtctaaactgacctctggtgtacc
gtcccgtttcaaaggctctggctctggtacggacttcactctgaccatctcctctctgcag
ccggaagactttgcaacgtactactgcggtggtggttactcttccatctctgacaccacgt
tcggtggtggcaccaaagttgaaatcaaacgtatgcatgaacaaaaactcatctcagaaga
ggatctgtaa

The above sequence is composed of the following

A26 gL8 (SEQ ID NO:78)
gatatccagatgacccagagtccaagcagtctctccgccagcgtaggcgatcgtgtgacta
ttacctgtcgtgcaacccagagcatctacaacgctctggcttggtatcagcagaaaccggg
taaagcgccaaaactcctgatctacaacgcgaacactctgcataccggtgttccgtctcgt
ttctctgcgtctggttctggtacggactctactctgaccatctcctctctgcagccggaag
atttcgcgacctactactgccagcagtactacgattacccactgacgtttggtggtggtac
caaagttgagatcaaa
DIQMTQSPSSLSASVGDRVTITCRATQSIYNALAWYQQKPGKAPKLLIYNANTLHTGVPSR
FSASGSGTDSTLTISSLQPEDFATYYCQQYYDYPLTFGGGTKVEIK (SEQ ID NO:79)

CK (SEQ ID NO:80)
cgtacggttgcagctccatccgtcttcatctttccaccgtctgacgaacagctcaaatctg
gtactgcttctgtcgtttgcctcctgaacaacttctatccgcgtgaagcgaaagtccagtg
gaaagtcgacaacgcactccagtctggtaactctcaggaatctgtgaccgaacaggactcc
aaagactccacctactctctgtctagcaccctgactctgtccaaagcagactacgagaaac
acaaagtgtacgcttgcgaagttacccatcagggtctgagctctccggttaccaaaagctt
taatagaggggagtgt
RTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC (SEQ ID NO:81)

2G4S
Tccggaggcggtggctctggtggcggtggatcc (SEQ ID NO:71)
SGGGGSGGGS (SEQ ID NO:72)

Figure 7

645 gL1
Gatatcgtgatgacccagagtccaagcagtgtttccgccagcgtaggcgatcgtgtgactat
tacctgtcagtcctctccgagcgtttggtccaacttcctgagctggtaccagcagaaaccgg
gtaaagccccgaaactgctgatctacgaggcgtctaaactgacctctggtgtaccgtcccgt
ttcaaaggctctggctctggtacggacttcactctgaccatctcctctctgcagccggaaga
ctttgcaacgtactactgcggtggtggttactcttccatctctgacaccacgttcggtggtg
gcaccaaagttgaaatcaaacgt (SEQ ID NO:82)

DIVMTQSPSSVSASVGDRVTITCQSSPSVWSNFLSWYQQKPGKAPKLLIYEASKLTSGVPSR
FKGSGSGTDFTLTISSLQPEDFATYYCGGGYSSISDTTFGGGTKVEIKR (SEQ ID NO:83)

c-myc tag
atgcatgaacaaaaactcatctcagaagaggatctg (SEQ ID NO:84)

MHEQKLISEEDL (SEQ ID NO:85)

Figure 9

A26 gH2 gamma1-CH1 2G4S645gH1gamma1 Fc (SEQ ID NO:86)

EVQLVESGGGLVQPGGSLRLSCAASGFTFTNYGIHWIRQAPGKGLEWVASISPSGGLTYYRD
SVKGRFTISRDDAKNSPYLQMNSLRAEDTAVYYCATGGEGIFDYWGQGTLVTVSSASTKGPS
VFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCSGGGGSGGGGSEVQLLESGGGLVQPGGS
LRLSCAVSGIDLSNYAINWVRQAPGKGLEWIGIIWASGTTFYATWAKGRFTISRDSTTVYLQ
MNSLRAEDTAVYYCARTVPGYSTAPYFDLWGQGTLVTVSSDKTHTCPPCPAPELLGGPSVFL
FPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSRWQQGNVFSCSVM
HEALHNHYTQKSLSLSPGK

Gamma 1 Fc (without hinge) (SEQ ID NO:87)
APELLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSR
WQQGNVFSCSVMHEALHNHYTQKSLSLSPGK

A26 gL8 C24GS 645gL1 (no myc tag) (SEQ ID NO:88)

DIQMTQSPSSLSASVGDRVTITCRATQSIYNALAWYQQKPGKAPKLLIYNANTLHTGVPSRF
SASGSGTDSTLTISSLQPEDFATYYCQQYYDYPLTFGGGTKVEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGECSGGGGSGGGGSDIVMTQSPSSVSASVGDRVTITC
QSSPSVWSNFLSWYQQKPGKAPKLLIYEASKLTSGVPSRFKGSGSGTDFTLTISSLQPEDFA
TYYCGGGYSSISDTTFGGGTKVEIKR

SEQUENCE LISTING

```
<160> NUMBER OF SEQ ID NOS: 88

<210> SEQ ID NO 1
<211> LENGTH: 8
<212> TYPE: PRT
<213> ORGANISM: Artificial sequence
<220> FEATURE:
<223> OTHER INFORMATION: Hinge sequence

<400> SEQUENCE: 1

Asp Lys Thr His Thr Cys Ala Ala
1               5

<210> SEQ ID NO 2
<211> LENGTH: 11
<212> TYPE: PRT
<213> ORGANISM: Artificial sequence
<220> FEATURE:
<223> OTHER INFORMATION: Hinge sequence

<400> SEQUENCE: 2

Asp Lys Thr His Thr Cys Pro Pro Cys Pro Ala
1               5                   10

<210> SEQ ID NO 3
<211> LENGTH: 18
<212> TYPE: PRT
<213> ORGANISM: Artificial sequence
<220> FEATURE:
<223> OTHER INFORMATION: Hinge sequence

<400> SEQUENCE: 3
```

```
Asp Lys Thr His Thr Cys Pro Pro Cys Pro Ala Thr Cys Pro Pro Cys
1               5                   10                  15

Pro Ala

<210> SEQ ID NO 4
<211> LENGTH: 25
<212> TYPE: PRT
<213> ORGANISM: Artificial sequence
<220> FEATURE:
<223> OTHER INFORMATION: Hinge sequence

<400> SEQUENCE: 4

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 5
<211> LENGTH: 30
<212> TYPE: PRT
<213> ORGANISM: Artificial sequence
<220> FEATURE:
<223> OTHER INFORMATION: Hinge sequence

<400> SEQUENCE: 5

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30

<210> SEQ ID NO 6
<211> LENGTH: 31
<212> TYPE: PRT
<213> ORGANISM: Artificial sequence
<220> FEATURE:
<223> OTHER INFORMATION: Hinge sequence

<400> SEQUENCE: 6

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 7
<211> LENGTH: 15
<212> TYPE: PRT
<213> ORGANISM: Artificial sequence
<220> FEATURE:
<223> OTHER INFORMATION: Hinge sequence

<400> SEQUENCE: 7

Asp Lys Thr His Thr Cys Cys Val Glu Cys Pro Pro Cys Pro Ala
1               5                   10                  15

<210> SEQ ID NO 8
<211> LENGTH: 26
<212> TYPE: PRT
<213> ORGANISM: Artificial sequence
<220> FEATURE:
<223> OTHER INFORMATION: Hinge sequence

<400> SEQUENCE: 8

Asp Lys Thr His Thr Cys Pro Arg Cys Pro Glu Pro Lys Ser Cys Asp
1               5                   10                  15
```

Thr Pro Pro Pro Cys Pro Arg Cys Pro Ala
            20                  25

<210> SEQ ID NO 9
<211> LENGTH: 11
<212> TYPE: PRT
<213> ORGANISM: Artificial sequence
<220> FEATURE:
<223> OTHER INFORMATION: Hinge sequence

<400> SEQUENCE: 9

Asp Lys Thr His Thr Cys Pro Ser Cys Pro Ala
1               5                   10

<210> SEQ ID NO 10
<211> LENGTH: 7
<212> TYPE: PRT
<213> ORGANISM: Artificial sequence
<220> FEATURE:
<223> OTHER INFORMATION: Linker

<400> SEQUENCE: 10

Ser Gly Gly Gly Gly Ser Glu
1               5

<210> SEQ ID NO 11
<211> LENGTH: 6
<212> TYPE: PRT
<213> ORGANISM: Artificial sequence
<220> FEATURE:
<223> OTHER INFORMATION: Linker

<400> SEQUENCE: 11

Asp Lys Thr His Thr Ser
1               5

<210> SEQ ID NO 12
<211> LENGTH: 6
<212> TYPE: PRT
<213> ORGANISM: Artificial sequence
<220> FEATURE:
<223> OTHER INFORMATION: Linker

<400> SEQUENCE: 12

Ser Gly Gly Gly Gly Ser
1               5

<210> SEQ ID NO 13
<211> LENGTH: 11
<212> TYPE: PRT
<213> ORGANISM: Artificial sequence
<220> FEATURE:
<223> OTHER INFORMATION: Linker

<400> SEQUENCE: 13

Ser Gly Gly Gly Gly Ser Gly Gly Gly Gly Ser
1               5                   10

<210> SEQ ID NO 14
<211> LENGTH: 16
<212> TYPE: PRT
<213> ORGANISM: Artificial sequence
<220> FEATURE:
<223> OTHER INFORMATION: Linker

<400> SEQUENCE: 14

```
Ser Gly Gly Gly Gly Ser Gly Gly Gly Gly Ser Gly Gly Gly Gly Ser
1               5                  10                  15
```

<210> SEQ ID NO 15
<211> LENGTH: 21
<212> TYPE: PRT
<213> ORGANISM: Artificial sequence
<220> FEATURE:
<223> OTHER INFORMATION: Linker

<400> SEQUENCE: 15

```
Ser Gly Gly Gly Gly Ser Gly Gly Gly Gly Ser Gly Gly Gly Gly Ser
1               5                  10                  15

Gly Gly Gly Gly Ser
            20
```

<210> SEQ ID NO 16
<211> LENGTH: 26
<212> TYPE: PRT
<213> ORGANISM: Artificial sequence
<220> FEATURE:
<223> OTHER INFORMATION: Linker

<400> SEQUENCE: 16

```
Ser Gly Gly Gly Gly Ser Gly Gly Gly Gly Ser Gly Gly Gly Gly Ser
1               5                  10                  15

Gly Gly Gly Gly Ser Gly Gly Gly Gly Ser
            20                  25
```

<210> SEQ ID NO 17
<211> LENGTH: 11
<212> TYPE: PRT
<213> ORGANISM: Artificial sequence
<220> FEATURE:
<223> OTHER INFORMATION: Linker

<400> SEQUENCE: 17

```
Ala Ala Ala Gly Ser Gly Gly Ala Ser Ala Ser
1               5                  10
```

<210> SEQ ID NO 18
<211> LENGTH: 16
<212> TYPE: PRT
<213> ORGANISM: Artificial sequence
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 18

```
Ala Ala Ala Gly Ser Gly Xaa Gly Gly Gly Ser Gly Ala Ser Ala Ser
1               5                  10                  15
```

<210> SEQ ID NO 19
<211> LENGTH: 21
<212> TYPE: PRT
<213> ORGANISM: Artificial sequence
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)

<223> OTHER INFORMATION: Xaa can be any naturally occurring amino acid

<400> SEQUENCE: 19

Ala Ala Ala Gly Ser Gly Xaa Gly Gly Gly Ser Xaa Gly Gly Gly Ser
1               5                   10                  15

Gly Ala Ser Ala Ser
            20

<210> SEQ ID NO 20
<211> LENGTH: 26
<212> TYPE: PRT
<213> ORGANISM: Artificial sequence
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 20

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 21
<211> LENGTH: 31
<212> TYPE: PRT
<213> ORGANISM: Artificial sequence
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 21

Ala Ala Ala Gly Ser Gly Xaa Gly Gly Gly Ser Xaa Gly Gly Gly Ser
1               5                   10                  15

Xaa Gly Gly Gly Ser Xaa Gly Gly Gly Ser Gly Ala Ser Ala Ser
            20                  25                  30

<210> SEQ ID NO 22
<211> LENGTH: 13
<212> TYPE: PRT
<213> ORGANISM: Artificial sequence
<220> FEATURE:
<223> OTHER INFORMATION: Linker
<220> FEATURE:
<221> NAME/KEY: misc_feature

```
<222> LOCATION: (7)..(7)
<223> OTHER INFORMATION: Xaa can be any naturally occurring amino acid

<400> SEQUENCE: 22

Ala Ala Ala Gly Ser Gly Xaa Ser Gly Ala Ser Ala Ser
1               5                  10

<210> SEQ ID NO 23
<211> LENGTH: 28
<212> TYPE: PRT
<213> ORGANISM: Artificial sequence
<220> FEATURE:
<223> OTHER INFORMATION: Linker

<400> SEQUENCE: 23

Pro Gly Gly Asn Arg Gly Thr Thr Thr Thr Arg Arg Pro Ala Thr Thr
1               5                  10                  15

Thr Gly Ser Ser Pro Gly Pro Thr Gln Ser His Tyr
            20                  25

<210> SEQ ID NO 24
<211> LENGTH: 11
<212> TYPE: PRT
<213> ORGANISM: Artificial sequence
<220> FEATURE:
<223> OTHER INFORMATION: Linker

<400> SEQUENCE: 24

Ala Thr Thr Thr Gly Ser Ser Pro Gly Pro Thr
1               5                  10

<210> SEQ ID NO 25
<211> LENGTH: 6
<212> TYPE: PRT
<213> ORGANISM: Artificial sequence
<220> FEATURE:
<223> OTHER INFORMATION: Linker

<400> SEQUENCE: 25

Ala Thr Thr Thr Gly Ser
1               5

<210> SEQ ID NO 26
<211> LENGTH: 21
<212> TYPE: PRT
<213> ORGANISM: Artificial sequence
<220> FEATURE:
<223> OTHER INFORMATION: Linker

<400> SEQUENCE: 26

Glu Pro Ser Gly Pro Ile Ser Thr Ile Asn Ser Pro Pro Ser Lys Glu
1               5                  10                  15

Ser His Lys Ser Pro
            20

<210> SEQ ID NO 27
<211> LENGTH: 15
<212> TYPE: PRT
<213> ORGANISM: Artificial sequence
<220> FEATURE:
<223> OTHER INFORMATION: Linker

<400> SEQUENCE: 27

Gly Thr Val Ala Ala Pro Ser Val Phe Ile Phe Pro Pro Ser Asp
1               5                  10                  15
```

```
<210> SEQ ID NO 28
<211> LENGTH: 15
<212> TYPE: PRT
<213> ORGANISM: Artificial sequence
<220> FEATURE:
<223> OTHER INFORMATION: Linker

<400> SEQUENCE: 28

Gly Gly Gly Gly Ile Ala Pro Ser Met Val Gly Gly Gly Gly Ser
1               5                   10                  15

<210> SEQ ID NO 29
<211> LENGTH: 15
<212> TYPE: PRT
<213> ORGANISM: Artificial sequence
<220> FEATURE:
<223> OTHER INFORMATION: Linker

<400> SEQUENCE: 29

Gly Gly Gly Gly Lys Val Glu Gly Ala Gly Gly Gly Gly Gly Ser
1               5                   10                  15

<210> SEQ ID NO 30
<211> LENGTH: 15
<212> TYPE: PRT
<213> ORGANISM: Artificial sequence
<220> FEATURE:
<223> OTHER INFORMATION: Linker

<400> SEQUENCE: 30

Gly Gly Gly Gly Ser Met Lys Ser His Asp Gly Gly Gly Gly Ser
1               5                   10                  15

<210> SEQ ID NO 31
<211> LENGTH: 15
<212> TYPE: PRT
<213> ORGANISM: Artificial sequence
<220> FEATURE:
<223> OTHER INFORMATION: Linker

<400> SEQUENCE: 31

Gly Gly Gly Gly Asn Leu Ile Thr Ile Val Gly Gly Gly Gly Ser
1               5                   10                  15

<210> SEQ ID NO 32
<211> LENGTH: 15
<212> TYPE: PRT
<213> ORGANISM: Artificial sequence
<220> FEATURE:
<223> OTHER INFORMATION: Linker

<400> SEQUENCE: 32

Gly Gly Gly Gly Val Val Pro Ser Leu Pro Gly Gly Gly Gly Ser
1               5                   10                  15

<210> SEQ ID NO 33
<211> LENGTH: 12
<212> TYPE: PRT
<213> ORGANISM: Artificial sequence
<220> FEATURE:
<223> OTHER INFORMATION: Linker

<400> SEQUENCE: 33

Gly Gly Glu Lys Ser Ile Pro Gly Gly Gly Gly Ser
1               5                   10
```

```
<210> SEQ ID NO 34
<211> LENGTH: 18
<212> TYPE: PRT
<213> ORGANISM: Artificial sequence
<220> FEATURE:
<223> OTHER INFORMATION: Linker

<400> SEQUENCE: 34

Arg Pro Leu Ser Tyr Arg Pro Pro Phe Pro Phe Gly Phe Pro Ser Val
1               5                   10                  15

Arg Pro

<210> SEQ ID NO 35
<211> LENGTH: 18
<212> TYPE: PRT
<213> ORGANISM: Artificial sequence
<220> FEATURE:
<223> OTHER INFORMATION: Linker

<400> SEQUENCE: 35

Tyr Pro Arg Ser Ile Tyr Ile Arg Arg His Pro Ser Pro Ser Leu
1               5                   10                  15

Thr Thr

<210> SEQ ID NO 36
<211> LENGTH: 18
<212> TYPE: PRT
<213> ORGANISM: Artificial sequence
<220> FEATURE:
<223> OTHER INFORMATION: Linker

<400> SEQUENCE: 36

Thr Pro Ser His Leu Ser His Ile Leu Pro Ser Phe Gly Leu Pro Thr
1               5                   10                  15

Phe Asn

<210> SEQ ID NO 37
<211> LENGTH: 18
<212> TYPE: PRT
<213> ORGANISM: Artificial sequence
<220> FEATURE:
<223> OTHER INFORMATION: Linker

<400> SEQUENCE: 37

Arg Pro Val Ser Pro Phe Thr Phe Pro Arg Leu Ser Asn Ser Trp Leu
1               5                   10                  15

Pro Ala

<210> SEQ ID NO 38
<211> LENGTH: 18
<212> TYPE: PRT
<213> ORGANISM: Artificial sequence
<220> FEATURE:
<223> OTHER INFORMATION: Linker

<400> SEQUENCE: 38

Ser Pro Ala Ala His Phe Pro Arg Ser Ile Pro Arg Pro Gly Pro Ile
1               5                   10                  15

Arg Thr

<210> SEQ ID NO 39
<211> LENGTH: 18
<212> TYPE: PRT
<213> ORGANISM: Artificial sequence
```

```
<220> FEATURE:
<223> OTHER INFORMATION: Linker

<400> SEQUENCE: 39

Ala Pro Gly Pro Ser Ala Pro Ser His Arg Ser Leu Pro Ser Arg Ala
1               5                   10                  15

Phe Gly

<210> SEQ ID NO 40
<211> LENGTH: 18
<212> TYPE: PRT
<213> ORGANISM: Artificial sequence
<220> FEATURE:
<223> OTHER INFORMATION: Linker

<400> SEQUENCE: 40

Pro Arg Asn Ser Ile His Phe Leu His Pro Leu Leu Val Ala Pro Leu
1               5                   10                  15

Gly Ala

<210> SEQ ID NO 41
<211> LENGTH: 18
<212> TYPE: PRT
<213> ORGANISM: Artificial sequence
<220> FEATURE:
<223> OTHER INFORMATION: Linker

<400> SEQUENCE: 41

Met Pro Ser Leu Ser Gly Val Leu Gln Val Arg Tyr Leu Ser Pro Pro
1               5                   10                  15

Asp Leu

<210> SEQ ID NO 42
<211> LENGTH: 18
<212> TYPE: PRT
<213> ORGANISM: Artificial sequence
<220> FEATURE:
<223> OTHER INFORMATION: Linker

<400> SEQUENCE: 42

Ser Pro Gln Tyr Pro Ser Pro Leu Thr Leu Thr Leu Pro Pro His Pro
1               5                   10                  15

Ser Leu

<210> SEQ ID NO 43
<211> LENGTH: 18
<212> TYPE: PRT
<213> ORGANISM: Artificial sequence
<220> FEATURE:
<223> OTHER INFORMATION: Linker

<400> SEQUENCE: 43

Asn Pro Ser Leu Asn Pro Pro Ser Tyr Leu His Arg Ala Pro Ser Arg
1               5                   10                  15

Ile Ser

<210> SEQ ID NO 44
<211> LENGTH: 17
<212> TYPE: PRT
<213> ORGANISM: Artificial sequence
<220> FEATURE:
<223> OTHER INFORMATION: Linker

<400> SEQUENCE: 44
```

```
Leu Pro Trp Arg Thr Ser Leu Leu Pro Ser Leu Pro Leu Arg Arg Arg
1               5                   10                  15

Pro
```

<210> SEQ ID NO 45
<211> LENGTH: 18
<212> TYPE: PRT
<213> ORGANISM: Artificial sequence
<220> FEATURE:
<223> OTHER INFORMATION: Linker

<400> SEQUENCE: 45

```
Pro Pro Leu Phe Ala Lys Gly Pro Val Gly Leu Leu Ser Arg Ser Phe
1               5                   10                  15

Pro Pro
```

<210> SEQ ID NO 46
<211> LENGTH: 18
<212> TYPE: PRT
<213> ORGANISM: Artificial sequence
<220> FEATURE:
<223> OTHER INFORMATION: Linker

<400> SEQUENCE: 46

```
Val Pro Pro Ala Pro Val Val Ser Leu Arg Ser Ala His Ala Arg Pro
1               5                   10                  15

Pro Tyr
```

<210> SEQ ID NO 47
<211> LENGTH: 17
<212> TYPE: PRT
<213> ORGANISM: Artificial sequence
<220> FEATURE:
<223> OTHER INFORMATION: Linker

<400> SEQUENCE: 47

```
Leu Arg Pro Thr Pro Pro Arg Val Arg Ser Tyr Thr Cys Cys Pro Thr
1               5                   10                  15

Pro
```

<210> SEQ ID NO 48
<211> LENGTH: 18
<212> TYPE: PRT
<213> ORGANISM: Artificial sequence
<220> FEATURE:
<223> OTHER INFORMATION: Linker

<400> SEQUENCE: 48

```
Pro Asn Val Ala His Val Leu Pro Leu Leu Thr Val Pro Trp Asp Asn
1               5                   10                  15

Leu Arg
```

<210> SEQ ID NO 49
<211> LENGTH: 18
<212> TYPE: PRT
<213> ORGANISM: Artificial sequence
<220> FEATURE:
<223> OTHER INFORMATION: Linker

<400> SEQUENCE: 49

```
Cys Asn Pro Leu Leu Pro Leu Cys Ala Arg Ser Pro Ala Val Arg Thr
1               5                   10                  15
```

Phe Pro

<210> SEQ ID NO 50
<211> LENGTH: 11
<212> TYPE: PRT
<213> ORGANISM: Artificial sequence
<220> FEATURE:
<223> OTHER INFORMATION: Albumin binding peptide

<400> SEQUENCE: 50

Asp Leu Cys Leu Arg Asp Trp Gly Cys Leu Trp
1               5                   10

<210> SEQ ID NO 51
<211> LENGTH: 11
<212> TYPE: PRT
<213> ORGANISM: Artificial sequence
<220> FEATURE:
<223> OTHER INFORMATION: Albumin binding peptide

<400> SEQUENCE: 51

Asp Ile Cys Leu Pro Arg Trp Gly Cys Leu Trp
1               5                   10

<210> SEQ ID NO 52
<211> LENGTH: 15
<212> TYPE: PRT
<213> ORGANISM: Artificial sequence
<220> FEATURE:
<223> OTHER INFORMATION: Albumin binding peptide

<400> SEQUENCE: 52

Met Glu Asp Ile Cys Leu Pro Arg Trp Gly Cys Leu Trp Gly Asp
1               5                   10                  15

<210> SEQ ID NO 53
<211> LENGTH: 20
<212> TYPE: PRT
<213> ORGANISM: Artificial sequence
<220> FEATURE:
<223> OTHER INFORMATION: Albumin binding peptide

<400> SEQUENCE: 53

Gln Arg Leu Met Glu Asp Ile Cys Leu Pro Arg Trp Gly Cys Leu Trp
1               5                   10                  15

Glu Asp Asp Glu
            20

<210> SEQ ID NO 54
<211> LENGTH: 20
<212> TYPE: PRT
<213> ORGANISM: Artificial sequence
<220> FEATURE:
<223> OTHER INFORMATION: Albumin binding peptide

<400> SEQUENCE: 54

Gln Gly Leu Ile Gly Asp Ile Cys Leu Pro Arg Trp Gly Cys Leu Trp
1               5                   10                  15

Gly Arg Ser Val
            20

<210> SEQ ID NO 55
<211> LENGTH: 21
<212> TYPE: PRT
<213> ORGANISM: Artificial sequence
<220> FEATURE:

<223> OTHER INFORMATION: Albumin binding peptide

<400> SEQUENCE: 55

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 56
<211> LENGTH: 15
<212> TYPE: PRT
<213> ORGANISM: Artificial sequence
<220> FEATURE:
<223> OTHER INFORMATION: Albumin binding peptide

<400> SEQUENCE: 56

Glu Asp Ile Cys Leu Pro Arg Trp Gly Cys Leu Trp Glu Asp Asp
1               5                   10                  15

<210> SEQ ID NO 57
<211> LENGTH: 18
<212> TYPE: PRT
<213> ORGANISM: Artificial sequence
<220> FEATURE:
<223> OTHER INFORMATION: Albumin binding peptide

<400> SEQUENCE: 57

Arg Leu Met Glu Asp Ile Cys Leu Pro Arg Trp Gly Cys Leu Trp Glu
1               5                   10                  15

Asp Asp

<210> SEQ ID NO 58
<211> LENGTH: 16
<212> TYPE: PRT
<213> ORGANISM: Artificial sequence
<220> FEATURE:
<223> OTHER INFORMATION: Albumin binding peptide

<400> SEQUENCE: 58

Met Glu Asp Ile Cys Leu Pro Arg Trp Gly Cys Leu Trp Glu Asp Asp
1               5                   10                  15

<210> SEQ ID NO 59
<211> LENGTH: 15
<212> TYPE: PRT
<213> ORGANISM: Artificial sequence
<220> FEATURE:
<223> OTHER INFORMATION: Albumin binding peptide

<400> SEQUENCE: 59

Met Glu Asp Ile Cys Leu Pro Arg Trp Gly Cys Leu Trp Glu Asp
1               5                   10                  15

<210> SEQ ID NO 60
<211> LENGTH: 18
<212> TYPE: PRT
<213> ORGANISM: Artificial sequence
<220> FEATURE:
<223> OTHER INFORMATION: Albumin binding peptide

<400> SEQUENCE: 60

Arg Leu Met Glu Asp Ile Cys Leu Ala Arg Trp Gly Cys Leu Trp Glu
1               5                   10                  15

Asp Asp

<210> SEQ ID NO 61
<211> LENGTH: 20
<212> TYPE: PRT
<213> ORGANISM: Artificial sequence
<220> FEATURE:
<223> OTHER INFORMATION: Albumin binding peptide

<400> SEQUENCE: 61

Glu Val Arg Ser Phe Cys Thr Arg Trp Pro Ala Glu Lys Ser Cys Lys
1               5                   10                  15

Pro Leu Arg Gly
            20

<210> SEQ ID NO 62
<211> LENGTH: 20
<212> TYPE: PRT
<213> ORGANISM: Artificial sequence
<220> FEATURE:
<223> OTHER INFORMATION: Albumin binding peptide

<400> SEQUENCE: 62

Arg Ala Pro Glu Ser Phe Val Cys Tyr Trp Glu Thr Ile Cys Phe Glu
1               5                   10                  15

Arg Ser Glu Gln
            20

<210> SEQ ID NO 63
<211> LENGTH: 11
<212> TYPE: PRT
<213> ORGANISM: Artificial sequence
<220> FEATURE:
<223> OTHER INFORMATION: Albumin binding peptide

<400> SEQUENCE: 63

Glu Met Cys Tyr Phe Pro Gly Ile Cys Trp Met
1               5                   10

<210> SEQ ID NO 64
<211> LENGTH: 11
<212> TYPE: PRT
<213> ORGANISM: Artificial sequence
<220> FEATURE:
<223> OTHER INFORMATION: Linker

<400> SEQUENCE: 64

Gly Ala Pro Ala Pro Ala Ala Pro Ala Pro Ala
1               5                   10

<210> SEQ ID NO 65
<211> LENGTH: 4
<212> TYPE: PRT
<213> ORGANISM: Artificial sequence
<220> FEATURE:
<223> OTHER INFORMATION: Linker

<400> SEQUENCE: 65

Pro Pro Pro Pro
1

<210> SEQ ID NO 66
<211> LENGTH: 2089
<212> TYPE: DNA
<213> ORGANISM: Artificial sequence
<220> FEATURE:
<223> OTHER INFORMATION: A26gH2 gamma1-CH1 2GS 645gH1 gamma1Fc

<400> SEQUENCE: 66

```
gaggtgcagc tggtcgagtc tggaggcggg cttgtccagc ctggagggag cctgcgtctc      60
tcttgtgcag caagcggttt cacgttcacc aactacggta tccactggat tcgtcaggca     120
ccaggtaaag gtctggaatg ggtagcctct atctctccgt ctggtggtct gacgtactac     180
cgtgactctg tcaaaggtcg tttcaccatc tctcgtgatg acgcgaaaaa ctctccgtac     240
ctgcagatga actctctgcg tgcagaagat accgcagtgt actactgcgc tactggtggt     300
gaaggtatct tcgactactg gggtcagggt accctggtaa ctgtctcgag cgcttctacc     360
aaaggtccga gcgttttccc actggctccg agctctaaat ccacctctgg tggtacggct     420
gcactgggtt gcctggtgaa agactacttc ccagaaccag ttaccgtgtc ttggaactct     480
ggtgcactga cctctggtgt tcacaccttt ccagcagttc tgcagtcttc tggtctgtac     540
tccctgtcta gcgtggttac cgttccgtct tcttctctgg gtactcagac ctacatctgc     600
aacgtcaacc acaaaccgtc caacacgaaa gtggacaaaa agtcgagcc gaaatcctgt     660
tccggaggtg gcggttctgg tggcggtgga tccgaggttc agctgctgga gtctggaggc     720
gggcttgtcc agcctggagg gagcctgcgt ctctcttgtg cagtaagcgg catcgacctg     780
tccaactacg cgattaactg ggtacgtcag gcaccggta aaggtctgga atggatcggc     840
atcatctggg cctctggtac gaccttctac gctacttggg ccaaaggtcg tttcaccatc     900
tcccgtgact ctaccaccgt gtacctgcag atgaactctc tgcgtgcgga agacactgcg     960
gtttactatt gcgcgcgtac cgttccgggc tattctactg caccgtactt cgacctgtgg    1020
ggtcagggta ctctggttac cgtctcgtct gacaaaactc acacatgccc accgtgccca    1080
ggtaagccag cccaggcctc gccctccagc tcaaggcggg acaggtgccc tagagtagcc    1140
tgcatccagg gacaggcccc agccgggtgc tgacacgtcc acctccatct cttcctcagc    1200
acctgaactc ctgggggac cgtcagtctt cctcttcccc ccaaaaccca aggacaccct    1260
catgatctcc cggacccctg aggtcacatg cgtggtggtg gacgtgagcc acgaagaccc    1320
tgaggtcaag ttcaactggt acgtggacgg cgtggaggtg cataatgcca agacaaagcc    1380
gcgggaggag cagtacaaca gcacgtaccg tgtggtcagc gtcctcaccg tcctgcacca    1440
ggactggctg aatggcaagg agtacaagtg caaggtctcc aacaaagccc tcccagcccc    1500
catcgagaaa accatctcca aagccaaagg tgggacccgt ggggtgcgag gccacatgg    1560
acagaggccg gctcggccca ccctctgccc tgagagtgac cgctgtacca acctctgtcc    1620
ctacagggca gccccgagaa ccacaggtgt acaccctgcc cccatcccgg gatgagctga    1680
ccaagaacca ggtcagcctg acctgcctgg tcaaaggctt ctatcccagc gacatcgccg    1740
tggagtggga gagcaatggg cagccggaga caactacaa gaccacgcct cccgtgctgg    1800
actccgacgg ctccttcttc ctctacagca agctcaccgt ggacaagagc aggtggcagc    1860
aggggaacgt cttctcatgc tccgtgatgc atgaggctct gcacaaccac tacacgcaga    1920
agagcctctc cctgtctccg ggtaaatgag tgcgacggcc ggcaagcccc cgctcccgg    1980
gctctcgcgg tcgcacgagg atgcttggca cgtaccccct gtacatactt cccgggcgcc    2040
cagcatggaa ataaagcacc cagcgctgcc ctgggccgag ctcgaattc               2089
```

<210> SEQ ID NO 67
<211> LENGTH: 351
<212> TYPE: DNA
<213> ORGANISM: Artificial sequence
<220> FEATURE:
<223> OTHER INFORMATION: A26gH2

<400> SEQUENCE: 67

```
gaggtgcagc tggtcgagtc tggaggcggg cttgtccagc ctggagggag cctgcgtctc    60
tcttgtgcag caagcggttt cacgttcacc aactacggta tccactggat tcgtcaggca   120
ccaggtaaag gtctggaatg gtagcctct atctctccgt ctggtggtct gacgtactac    180
cgtgactctg tcaaaggtcg tttcaccatc tctcgtgatg acgcgaaaaa ctctccgtac   240
ctgcagatga actctctgcg tgcagaagat accgcagtgt actactgcgc tactggtggt   300
gaaggtatct tcgactactg gggtcagggt accctggtaa ctgtctcgag c            351
```

<210> SEQ ID NO 68
<211> LENGTH: 117
<212> TYPE: PRT
<213> ORGANISM: Artificial sequence
<220> FEATURE:
<223> OTHER INFORMATION: A26 gH2

<400> SEQUENCE: 68

```
Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Thr Asn Tyr
             20                  25                  30
Gly Ile His Trp Ile Arg Gln Ala Pro Gly Lys Gly Leu Glu Trp Val
         35                  40                  45
Ala Ser Ile Ser Pro Ser Gly Gly Leu Thr Tyr Tyr Arg Asp Ser Val
     50                  55                  60
Lys Gly Arg Phe Thr Ile Ser Arg Asp Asp Ala Lys Asn Ser Pro Tyr
 65                  70                  75                  80
Leu Gln Met Asn Ser Leu Arg Ala Glu Asp Thr Ala Val Tyr Tyr Cys
                 85                  90                  95
Ala Thr Gly Gly Glu Gly Ile Phe Asp Tyr Trp Gly Gln Gly Thr Leu
            100                 105                 110
Val Thr Val Ser Ser
        115
```

<210> SEQ ID NO 69
<211> LENGTH: 309
<212> TYPE: DNA
<213> ORGANISM: Artificial sequence
<220> FEATURE:
<223> OTHER INFORMATION: gamma 1 cH1

<400> SEQUENCE: 69

```
gcttctacca aaggtccgag cgtttcccca ctggctccga gctctaaatc cacctctggt    60
ggtacggctg cactggggttg cctggtgaaa gactacttcc cagaaccagt accgtgtct   120
tggaactctg gtgcactgac ctctggtgtt cacacctttc cagcagttct gcagtcttct   180
ggtctgtact ccctgtctag cgtggttacc gttccgtctt cttctctggg tactcagacc   240
tacatctgca acgtcaacca caaaccgtcc aacacgaaag tggacaaaaa agtcgagccg   300
aaatcctgt                                                          309
```

<210> SEQ ID NO 70
<211> LENGTH: 103
<212> TYPE: PRT
<213> ORGANISM: Artificial sequence
<220> FEATURE:
<223> OTHER INFORMATION: gamma 1 CH1

<400> SEQUENCE: 70

| Ala | Ser | Thr | Lys | Gly | Pro | Ser | Val | Phe | Pro | Leu | Ala | Pro | Ser | Ser | Lys |
|---|---|---|---|---|---|---|---|---|---|---|---|---|---|---|---|
| 1 | | | | 5 | | | | | 10 | | | | | 15 | |

| Ser | Thr | Ser | Gly | Gly | Thr | Ala | Ala | Leu | Gly | Cys | Leu | Val | Lys | Asp | Tyr |
|---|---|---|---|---|---|---|---|---|---|---|---|---|---|---|---|
| | | | 20 | | | | | 25 | | | | | 30 | | |

| Phe | Pro | Glu | Pro | Val | Thr | Val | Ser | Trp | Asn | Ser | Gly | Ala | Leu | Thr | Ser |
|---|---|---|---|---|---|---|---|---|---|---|---|---|---|---|---|
| | | 35 | | | | | 40 | | | | | 45 | | | |

| Gly | Val | His | Thr | Phe | Pro | Ala | Val | Leu | Gln | Ser | Ser | Gly | Leu | Tyr | Ser |
|---|---|---|---|---|---|---|---|---|---|---|---|---|---|---|---|
| | 50 | | | | | 55 | | | | | 60 | | | | |

| Leu | Ser | Ser | Val | Val | Thr | Val | Pro | Ser | Ser | Ser | Leu | Gly | Thr | Gln | Thr |
|---|---|---|---|---|---|---|---|---|---|---|---|---|---|---|---|
| 65 | | | | | 70 | | | | | 75 | | | | | 80 |

| Tyr | Ile | Cys | Asn | Val | Asn | His | Lys | Pro | Ser | Asn | Thr | Lys | Val | Asp | Lys |
|---|---|---|---|---|---|---|---|---|---|---|---|---|---|---|---|
| | | | | 85 | | | | | 90 | | | | | 95 | |

| Lys | Val | Glu | Pro | Lys | Ser | Cys |
|---|---|---|---|---|---|---|
| | | | 100 | | | |

<210> SEQ ID NO 71
<211> LENGTH: 33
<212> TYPE: DNA
<213> ORGANISM: Artificial sequence
<220> FEATURE:
<223> OTHER INFORMATION: 2G4S linker

<400> SEQUENCE: 71

```
tccggaggtg gcggttctgg tggcggtgga tcc                                  33
```

<210> SEQ ID NO 72
<211> LENGTH: 11
<212> TYPE: PRT
<213> ORGANISM: Artificial sequence
<220> FEATURE:
<223> OTHER INFORMATION: 2G4S linker

<400> SEQUENCE: 72

| Ser | Gly | Gly | Gly | Gly | Ser | Gly | Gly | Gly | Gly | Ser |
|---|---|---|---|---|---|---|---|---|---|---|
| 1 | | | | 5 | | | | | 10 | |

<210> SEQ ID NO 73
<211> LENGTH: 357
<212> TYPE: DNA
<213> ORGANISM: Artificial sequence
<220> FEATURE:
<223> OTHER INFORMATION: 645 gH1

<400> SEQUENCE: 73

```
gaggttcagc tgctggagtc tggaggcggg cttgtccagc ctggagggag cctgcgtctc      60
tcttgtgcag taagcggcat cgacctgtcc aactacgcga ttaactgggt acgtcaggca     120
ccgggtaaag gtctggaatg gatcggcatc atctgggcct tggtacgac cttctacgct      180
acttgggcca aggtcgtttt caccatctcc cgtgactcta ccaccgtgta cctgcagatg     240
aactctctgc gtgcggaaga cactgcggtt tactattgcg cgcgtaccgt tccgggctat     300
tctactgcac cgtacttcga cctgtggggt cagggtactc tggttaccgt ctcgtct       357
```

<210> SEQ ID NO 74
<211> LENGTH: 119
<212> TYPE: PRT
<213> ORGANISM: Artificial sequence
<220> FEATURE:
<223> OTHER INFORMATION: 645 gH1

<400> SEQUENCE: 74

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
50                  55                  60

Gly Arg Phe Thr Ile Ser Arg Asp Ser Thr Thr Val Tyr Leu Gln Met
65                  70                  75                  80

Asn Ser Leu Arg Ala Glu Asp Thr Ala Val Tyr Tyr Cys Ala Arg Thr
                85                  90                  95

Val Pro Gly Tyr Ser Thr Ala Pro Tyr Phe Asp Leu Trp Gly Gln Gly
            100                 105                 110

Thr Leu Val Thr Val Ser Ser
        115
```

<210> SEQ ID NO 75
<211> LENGTH: 899
<212> TYPE: DNA
<213> ORGANISM: Artificial sequence
<220> FEATURE:
<223> OTHER INFORMATION: Gamma1 Fc (hinge CH2CH3)

<400> SEQUENCE: 75

```
gacaaaactc acacatgccc accgtgccca ggtaagccag cccaggcctc gccctccagc    60
tcaaggcggg acaggtgccc tagagtagcc tgcatccagg acaggcccc agccgggtgc   120
tgacacgtcc acctccatct cttcctcagc acctgaactc ctgggggac cgtcagtctt   180
cctcttcccc ccaaaaccca aggacaccct catgatctcc cggacccctg aggtcacatg   240
cgtggtggtg gacgtgagcc acgaagaccc tgaggtcaag ttcaactggt acgtggacgg   300
cgtggaggtg cataatgcca agacaaagcc gcgggaggag cagtacaaca gcacgtaccg   360
tgtggtcagc gtcctcaccg tcctgcacca ggactggctg aatggcaagg agtacaagtg   420
caaggtctcc aacaaagccc tcccagcccc catcgagaaa accatctcca aagccaaagg   480
tgggacccgt ggggtgcgag ggccacatgg acagaggccg gctcggccca ccctctgccc   540
tgagagtgac cgctgtacca acctctgtcc ctacagggca gccccgagaa ccacaggtgt   600
acaccctgcc cccatcccgg gatgagctga ccaagaacca ggtcagcctg acctgcctgg   660
tcaaaggctt ctatcccagc gacatcgccg tggagtggga gagcaatggg cagccggaga   720
acaactacaa gaccacgcct cccgtgctgg actccgacgg ctccttcttc ctctacagca   780
agctcaccgt ggacaagagc aggtggcagc aggggaacgt cttctcatgc tccgtgatgc   840
atgaggctct gcacaaccac tacacgcaga agagcctctc cctgtctccg ggtaaatga   899
```

<210> SEQ ID NO 76
<211> LENGTH: 227
<212> TYPE: PRT
<213> ORGANISM: Artificial sequence
<220> FEATURE:
<223> OTHER INFORMATION: Gamma 1Fc (hinge CH2 CH3)

<400> SEQUENCE: 76

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
```

```
              20                  25                  30
Ile Ser Arg Thr Pro Glu Val Thr Cys Val Val Asp Val Ser His
         35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
            130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
            210                 215                 220
Pro Gly Lys
225

<210> SEQ ID NO 77
<211> LENGTH: 1047
<212> TYPE: DNA
<213> ORGANISM: Artificial sequence
<220> FEATURE:
<223> OTHER INFORMATION: A26gL8 cK 2G4S 645gL1 c-myc tag

<400> SEQUENCE: 77
gatatccaga tgacccagag tccaagcagt ctctccgcca gcgtaggcga tcgtgtgact      60
attacctgtc gtgcaaccca gagcatctac aacgctctgg cttggtatca gcagaaaccg     120
ggtaaagcgc caaaactcct gatctacaac gcgaacactc tgcataccgg tgttccgtct     180
cgtttctctg cgtctggttc tggtacggac tctactctga ccatctcctc tctgcagccg     240
gaagatttcg cgacctacta ctgccagcag tactacgatt acccactgac gtttggtggt     300
ggtaccaaag ttgagatcaa acgtacggtt gcagctccat ccgtcttcat ctttccaccg     360
tctgacgaac agctcaaatc tggtactgct tctgtcgttt gcctcctgaa caacttctat     420
ccgcgtgaag cgaaagtcca gtggaaagtc gacaacgcac tccagtctgg taactctcag     480
gaatctgtga ccgaacagga ctccaaagac tccacctact ctctgtctag caccctgact     540
ctgtccaaag cagactacga aaacacaaa gtgtacgctt gcgaagttac ccatcagggt     600
ctgagctctc cggttaccaa aagctttaat agaggggagt gttccggagg cggtggctct     660
ggtggcggtg gatccgatat cgtgatgacc cagagtccaa gcagtgtttc gccagcgta      720
ggcgatcgtg tgactattac ctgtcagtcc tctccgagcg tttggtccaa cttcctgagc     780
tggtaccagc agaaaccggg taaagccccg aaactgctga tctacgaggc gtctaaactg     840
```

```
acctctggtg taccgtcccg tttcaaaggc tctggctctg gtacggactt cactctgacc    900
atctcctctc tgcagccgga agactttgca acgtactact gcggtggtgg ttactcttcc    960
atctctgaca ccacgttcgg tggtggcacc aaagttgaaa tcaaacgtat gcatgaacaa   1020
aaactcatct cagaagagga tctgtaa                                       1047
```

<210> SEQ ID NO 78
<211> LENGTH: 321
<212> TYPE: DNA
<213> ORGANISM: Artificial sequence
<220> FEATURE:
<223> OTHER INFORMATION: A26 gL8

<400> SEQUENCE: 78

```
gatatccaga tgacccagag tccaagcagt ctctccgcca gcgtaggcga tcgtgtgact     60
attacctgtc gtgcaaccca gagcatctac aacgctctgg cttggtatca gcagaaaccg    120
ggtaaagcgc caaaactcct gatctacaac gcgaacactc tgcataccgg tgttccgtct    180
cgtttctctg cgtctggttc tggtacggac tctactctga ccatctcctc tctgcagccg    240
gaagatttcg cgacctacta ctgccagcag tactacgatt acccactgac gtttggtggt    300
ggtaccaaag ttgagatcaa a                                              321
```

<210> SEQ ID NO 79
<211> LENGTH: 107
<212> TYPE: PRT
<213> ORGANISM: Artificial sequence
<220> FEATURE:
<223> OTHER INFORMATION: A26 gL8

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys
            100                 105

<210> SEQ ID NO 80
<211> LENGTH: 321
<212> TYPE: DNA
<213> ORGANISM: Artificial sequence
<220> FEATURE:
<223> OTHER INFORMATION: cKappa

<400> SEQUENCE: 80

```
cgtacggttg cagctccatc cgtcttcatc tttccaccgt ctgacgaaca gctcaaatct     60
ggtactgctt ctgtcgtttg cctcctgaac aacttctatc cgcgtgaagc gaaagtccag    120
tggaaagtcg acaacgcact ccagtctggt aactctcagg aatctgtgac cgaacaggac    180
tccaaagact ccacctactc tctgtctagc accctgactc tgtccaaagc agactacgag    240
```

```
aaacacaaag tgtacgcttg cgaagttacc catcagggtc tgagctctcc ggttaccaaa     300
agctttaata gagggagtg t                                                321
```

<210> SEQ ID NO 81
<211> LENGTH: 107
<212> TYPE: PRT
<213> ORGANISM: Artificial sequence
<220> FEATURE:
<223> OTHER INFORMATION: Ckappa

<400> SEQUENCE: 81

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 82
<211> LENGTH: 333
<212> TYPE: DNA
<213> ORGANISM: Artificial sequence
<220> FEATURE:
<223> OTHER INFORMATION: 645gL1

<400> SEQUENCE: 82

```
gatatcgtga tgacccagag tccaagcagt gtttccgcca gcgtaggcga tcgtgtgact     60
attacctgtc agtcctctcc gagcgtttgg tccaacttcc tgagctggta ccagcagaaa    120
ccgggtaaag ccccgaaact gctgatctac gaggcgtcta aactgacctc tggtgtaccg    180
tcccgtttca aaggctctgg ctctggtacg gacttcactc tgaccatctc ctctctgcag    240
ccggaagact ttgcaacgta ctactgcggt ggtggttact cttccatctc tgacaccacg    300
ttcggtggtg gcaccaaagt tgaaatcaaa cgt                                 333
```

<210> SEQ ID NO 83
<211> LENGTH: 111
<212> TYPE: PRT
<213> ORGANISM: Artificial sequence
<220> FEATURE:
<223> OTHER INFORMATION: 645gL1

<400> SEQUENCE: 83

```
Asp Ile Val Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Lys
    50                  55                  60
```

```
Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gly Gly Gly Tyr Ser Ser Ile
                 85                  90                  95

Ser Asp Thr Thr Phe Gly Gly Gly Thr Lys Val Glu Ile Lys Arg
                100                 105                 110
```

<210> SEQ ID NO 84
<211> LENGTH: 36
<212> TYPE: DNA
<213> ORGANISM: Artificial sequence
<220> FEATURE:
<223> OTHER INFORMATION: Myc tag

<400> SEQUENCE: 84
atgcatgaac aaaaactcat ctcagaagag gatctg                              36

<210> SEQ ID NO 85
<211> LENGTH: 12
<212> TYPE: PRT
<213> ORGANISM: Artificial sequence
<220> FEATURE:
<223> OTHER INFORMATION: Myc tag

<400> SEQUENCE: 85

```
Met His Glu Gln Lys Leu Ile Ser Glu Glu Asp Leu
 1               5                  10
```

<210> SEQ ID NO 86
<211> LENGTH: 577
<212> TYPE: PRT
<213> ORGANISM: Artificial sequence
<220> FEATURE:
<223> OTHER INFORMATION: A26gH2 gamma1-CH1 2GS 645gH1 gamma1Fc

<400> SEQUENCE: 86

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Tyr
                 20                  25                  30

Gly Ile His Trp Ile Arg Gln Ala Pro Gly Lys Gly Leu Glu Trp Val
             35                  40                  45

Ala Ser Ile Ser Pro Ser Gly Leu Thr Tyr Tyr Arg Asp Ser Val
         50                  55                  60

Lys Gly Arg Phe Thr Ile Ser Arg Asp Asp Ala Lys Asn Ser Pro Tyr
 65                  70                  75                  80

Leu Gln Met Asn Ser Leu Arg Ala Glu Asp Thr Ala Val Tyr Tyr Cys
                 85                  90                  95

Ala Thr Gly Gly Glu Gly Ile Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Ser Gly Gly Gly
210                 215                 220

Gly Ser Gly Gly Gly Ser Glu Val Gln Leu Leu Glu Ser Gly Gly
225                 230                 235                 240

Gly Leu Val Gln Pro Gly Gly Ser Leu Arg Leu Ser Cys Ala Val Ser
                245                 250                 255

Gly Ile Asp Leu Ser Asn Tyr Ala Ile Asn Trp Val Arg Gln Ala Pro
                260                 265                 270

Gly Lys Gly Leu Glu Trp Ile Gly Ile Ile Trp Ala Ser Gly Thr Thr
            275                 280                 285

Phe Tyr Ala Thr Trp Ala Lys Gly Arg Phe Thr Ile Ser Arg Asp Ser
        290                 295                 300

Thr Thr Val Tyr Leu Gln Met Asn Ser Leu Arg Ala Glu Asp Thr Ala
305                 310                 315                 320

Val Tyr Tyr Cys Ala Arg Thr Val Pro Gly Tyr Ser Thr Ala Pro Tyr
                325                 330                 335

Phe Asp Leu Trp Gly Gln Gly Thr Leu Val Thr Val Ser Ser Asp Lys
            340                 345                 350

Thr His Thr Cys Pro Pro Cys Pro Ala Pro Glu Leu Leu Gly Gly Pro
        355                 360                 365

Ser Val Phe Leu Phe Pro Pro Lys Pro Lys Asp Thr Leu Met Ile Ser
370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Asp Glu Leu Thr Lys Asn Gln Val Ser Leu Thr
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys

<210> SEQ ID NO 87
<211> LENGTH: 217
<212> TYPE: PRT
```

<213> ORGANISM: Artificial sequence
<220> FEATURE:
<223> OTHER INFORMATION: gamma 1 Fc (CH2CH3)

<400> SEQUENCE: 87

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 88
<211> LENGTH: 336
<212> TYPE: PRT
<213> ORGANISM: Artificial sequence
<220> FEATURE:
<223> OTHER INFORMATION: A26gL8 C2G4S 645gL1 (no myc tag)

<400> SEQUENCE: 88

```
Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Gly Gly Gly Ser Gly Gly Gly Gly
        210                 215                 220

Ser Asp Ile Val Met Thr Gln Ser Pro Ser Ser Val Ser Ala Ser Val
225                 230                 235                 240

Gly Asp Arg Val Thr Ile Thr Cys Gln Ser Ser Pro Ser Val Trp Ser
                245                 250                 255

Asn Phe Leu Ser Trp Tyr Gln Gln Lys Pro Gly Lys Ala Pro Lys Leu
            260                 265                 270

Leu Ile Tyr Glu Ala Ser Lys Leu Thr Ser Gly Val Pro Ser Arg Phe
        275                 280                 285

Lys Gly Ser Gly Ser Gly Thr Asp Phe Thr Leu Thr Ile Ser Ser Leu
        290                 295                 300

Gln Pro Glu Asp Phe Ala Thr Tyr Tyr Cys Gly Gly Gly Tyr Ser Ser
305                 310                 315                 320

Ile Ser Asp Thr Thr Phe Gly Gly Gly Thr Lys Val Glu Ile Lys Arg
                325                 330                 335
```

MULTIVALENT ANTIBODIES

The present disclosure relates to antibodies with two antigen binding sites, for example wherein the steric hinderence around each site is minimized, such that affinity to the target antigen or antigens is not detrimentally affected by the format provided herein.

Multivalent antibodies are known. However, even though the basic concept was disclosed a number of years ago, there have been practical difficulties associated with exploiting the technology and thus it has not been widely adopted for the preparation of pharmaceutical biologic products in development.

A non-natural/non-native antibody format can be difficult to express, which may significantly increase the cost of goods to an untenable level. The formats may increase the immunogenicity or reduce the in vivo stability in comparison to a standard antibody or fragment and/or may have undesirable pharmokinetics.

In particular the problems associated with preparing homogenous products have been a concern for non-natural formats. If, for example, there is more than one permutation for combining the component monomers then mixtures can result. Thus elaborate purification methods may be required to isolate the desired/target entity at satisfactory purity levels.

This has been addressed in a number of ways, for example using short linkers in the production of bispecific diabodies was said to aid appropriate dimerisation. However, data has shown that the orientation of the variable domains can influence expression of the format and the formation of active binding sites.

One approach to force the assembly in the desired arrangement or orientation is referred to as the "knob-in-hole" method, in which a large "knob" is introduced in the VH domain by, for example in some antibodies exchanging valine 137 with the large residue phenyl alanine and replacing leucine 45 with tryptophan. A complementary hole can be introduced, for example in the VL domain by in some antibodies mutating phenylalanine 98 to methionine and tryptophan 87 to alanine. However, reduced antigen-binding activity was observed for several constructs.

WO2007/024715 tries to address one or more of these problems by providing a multivalent multispecific antibody (DVD-Ig) of the type shown in FIG. 1. The DVD-Igs are characterized in that the variable domain of the Va is linked directly to the variable domain Vb, for example by an amino acid or peptide.

However, it is now thought by the present inventors that in vivo the binding of the Va in this arrangement may be compromised because when antigen is bound to the Vb domain then the steric effects of the bound antigen reduce accessibility of Va to antigen and thus the ability of the latter to bind antigen is reduced. If antigen binds to Va then the reverse may also be true.

Simply increasing linker length between Va and Vb may simply increase the frequency/possibility for inappropriate dimerisations, leading to increased waste of starting materials and the need for more extensive purification.

In the present invention generally in any one chain a constant region fragment comprising at least CH1 or CL is provided between the position corresponding to Va and Vb. It is believed that the format according to the disclosure can provide good levels of expression because it is primarily composed of natural antibody components. What is more it is believed that the steric problem associated with the blocking of Va by antigen binding at Vb is avoided by providing at least a constant region fragment as a spacer.

Thus there is provided a recombinant antibody or a heavy/light chain component thereof comprising:
- a heavy chain comprising a constant region fragment,
- said constant region fragment located between two variable domains,
- the heavy chain further comprising an Fc region with at least one domain selected from CH2, CH3 and combinations thereof,
- with the proviso that the heavy chain contains no more than one CH1 domain and only contains two variable domains, and
- a light chain comprising a constant region fragment located between two variable domains, wherein said heavy and light chains are aligned one with the other to provide a first binding-site formed by a first pair of variable domains and a second binding-site formed by a second pair of variable domains.

In the first format there is a disulphide bond in the second cognate pair.

In the second format there is a disulphide bond in the first cognate pair.

In the third format there is a disulphide bond in the first and second cognate pair In the fourth format there is a disulphide bond in the second cognate pair and between the CH and CL constant region fragments.

In the fifth format there is a disulphide bond between the CH and CL constant region fragment.

Each of the heavy/light chain components shown can be associated with another such component to provide an antibody of the present disclosure.

Each of the first, second and third formats may also be provided in a format with a disulfide bond in the constant region.

Figure 1:
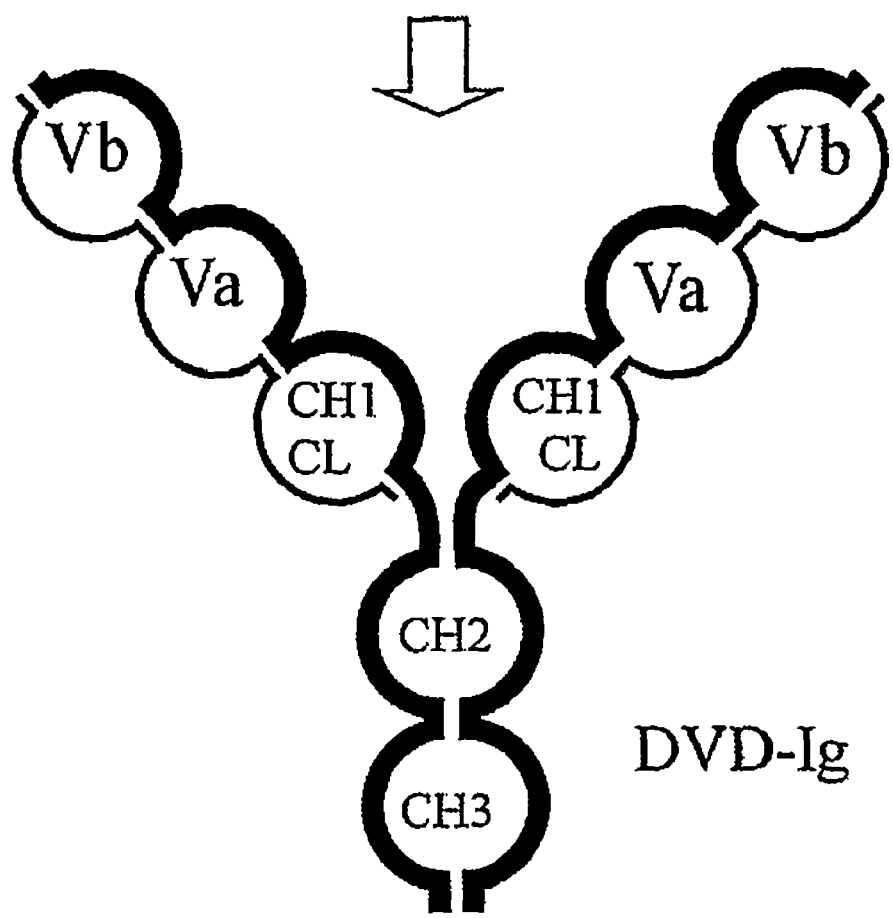
FIG. 1 shows a prior art antibody known as a DVD-Ig containing heavy and light chains
Figure 2:
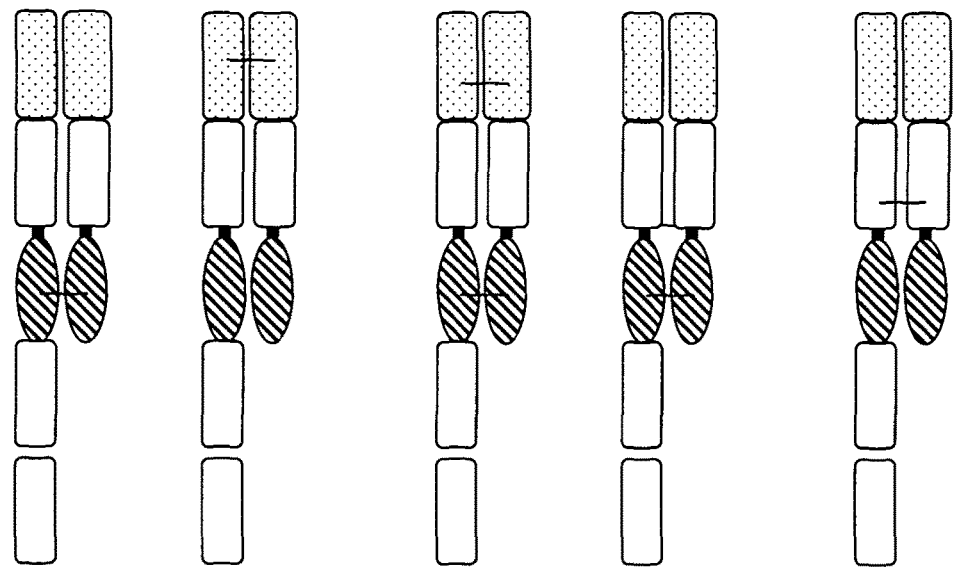
FIG. 2 shows five different heavy/light chain components of five different antibody formats according to the present invention comprising a first cognate pair wherein VH thereof is fused to a CH1 fragment and the VL thereof is fused to CL fragment. The CH1 and CL fragments are also linked via a peptide to a further VH or VL, as appropriate, of a second cognate pair. The heavy chain further comprises a CH2CH3 fragment.
Figure 3A:
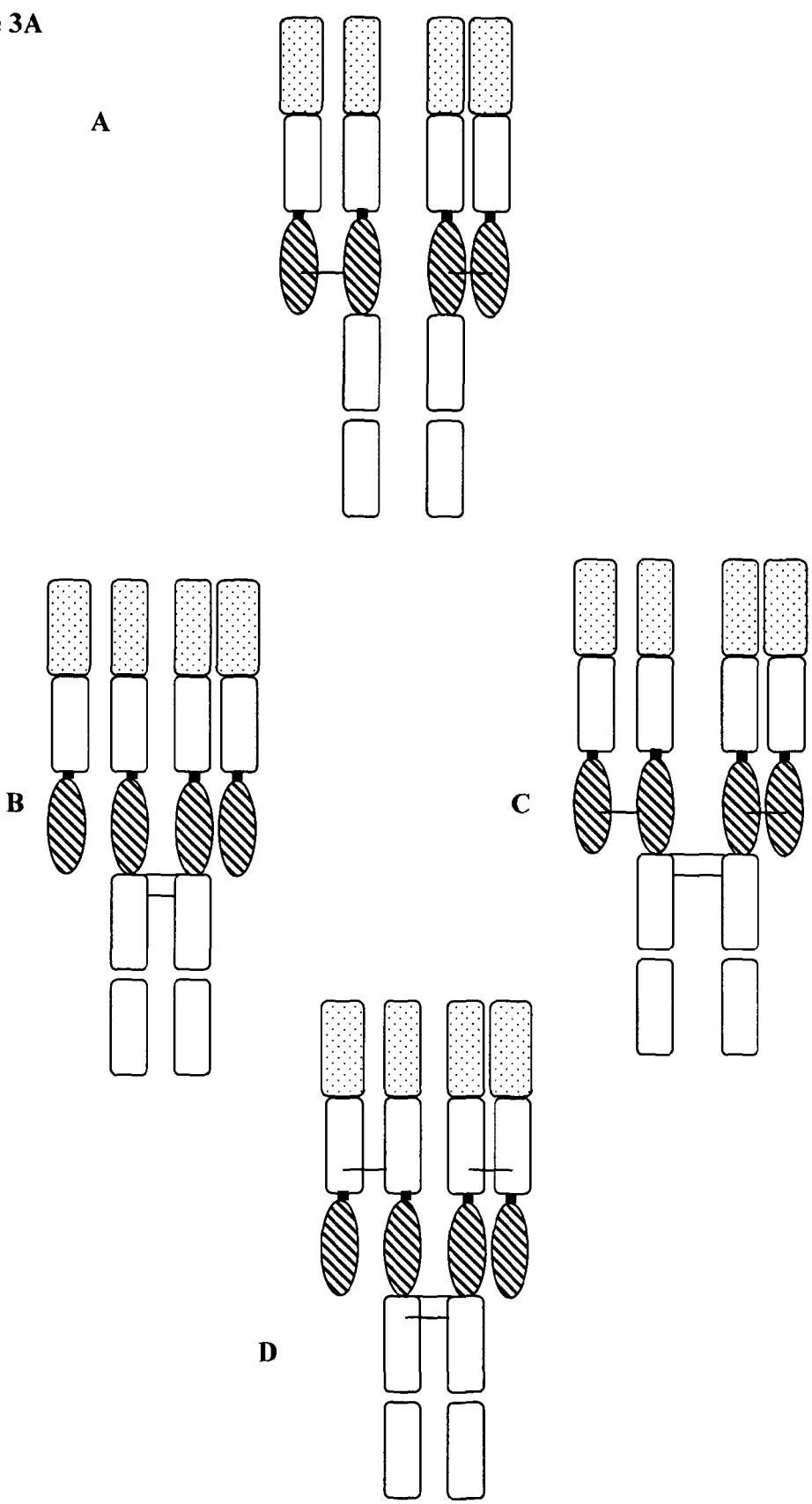

FIG. 3A A shows an antibody format according to the present disclosure wherein there is a disulfide stabilization between the second one pair of variable domains.

B shows an antibody format according to the present disclosure wherein there is a disulfide stabilization between the Fc hinge fragments.

C shows an antibody format according to the present disclosure with disulfide stabilization between the one pair of variable domains and the Fc hinge fragments of the antibody.

D shows an antibody format according to the present disclosure with disulfide bonds in the constant region and also the Fc region.

FIG. 3B E shows a heavy/light chain component format according to the present disclosure wherein the Fc region comrpises CH2CH3linkerCH2CH3. The format has a disulfide bond between variable domains of second cognate pair and also has one between the two CH2 domains or hinge regions.

F shows a heavy/light chain component format according to the present disclosure wherein the Fc region comprises CH2CH3linkerCH2CH3. The format also has a disulfide bond between the CH and CL domains and also has one between the two CH2 domains or hinge regions.

G shows an antibody format according to the present disclosure with disulfide bonds between the CH and CL constant region, one variable domain pair, and also the Fc hinge region.

H shows an antibody format according to the present disclosure with disulfide bonds between the CH and CL constant region and also in one pair of variable domains in each heavy/light chain component.

FIG. 4-7 show antibody sequences and fragments thereof

Figure 8:
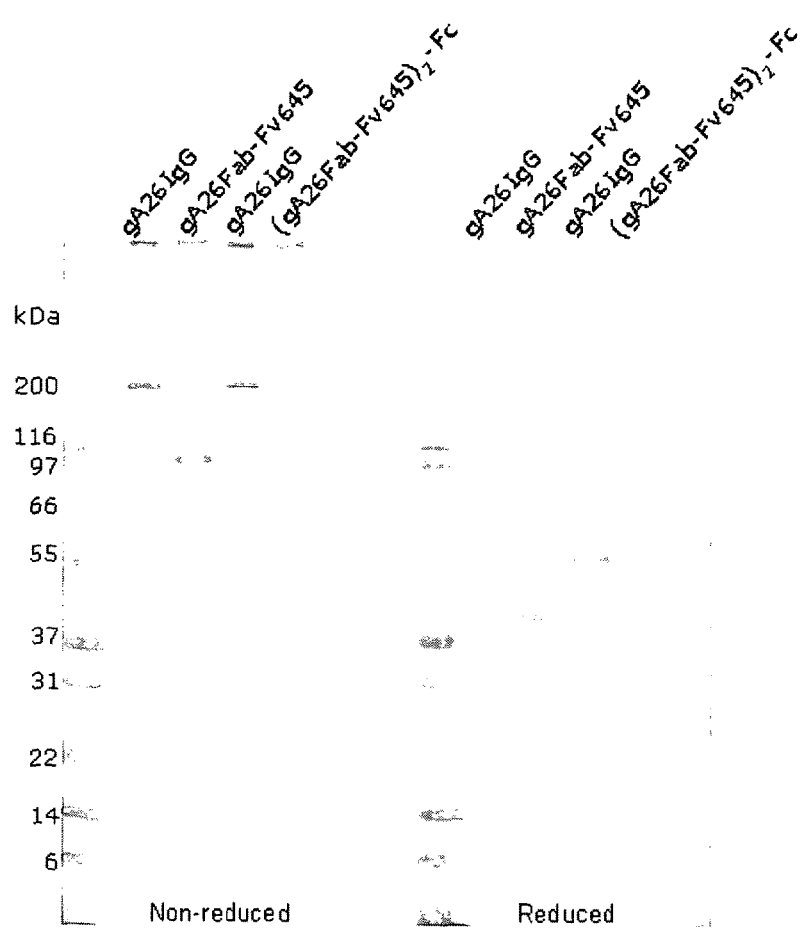

FIG. 8 shows an SDS page analysis of antibodies according the invention

FIG. 9 show antibody sequences and fragments thereof

In one alternative arrangement CL in the light chain is replaced by CH1 and the heavy chain is provided with a CL, for example replacing a CH1 domain therein.

Antibody as employed herein is intended to refer to format comprising two heavy chains and two light chains, in the traditional Y-type arrangement characteristic of antibodies.

A heavy/light chain component according to the present disclosure is a heavy chain and associated light chain.

The heavy chain as employed herein is the chain which comprises the Fc region.

The light chain as employed herein does not comprise an Fc region.

The variable domains are provided in each chain such that they form pre-defined pairs with suitable/adequate binding to a target antigen.

Suitable variable domains pairs may be identified by any means possible, for example including generation of antibodies in hosts and screening of B cells. Alternatively suitable pairs may be identified by phage display. In one embodiment the variable domain pair has affinity for a target antigen of 100 nM or less, such as 50 nM or less, in particular 1 nM or less.

Phage display methods known in the art and include those disclosed by Brinkman et al., *J. Immunol. Methods,* 1995, 182, 41-50; Ames et al., *J. Immunol. Methods,* 1995, 184, 177-186; Kettleborough et al. *Eur. J. Immunol.,* 1994, 24, 952-958; Persic et al., *Gene,* 1997 187, 9-18; and Burton et al., *Advances in Immunology,* 1994, 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

Transgenic mice, or other organisms, including other mammals, may be used to generate humanized antibodies.

In one embodiment the variable domain pair is a cognate pair.

Cognate pair as employed herein is intended to refer to a natural pair of variable domains, that is to say isolated from a single antibody or antibody expressing cell.

In one example the cognate pair are a complementary VH/VL pair which bind the antigen co-operatively i.e. they are a complementary VH/VL pair.

In one example the VH/VL pair are monospecific.

Typically they will be a VH/VL pair derived from the same antibody.

In one example the cognate pair are a pair of variable domains isolated as a pair from a 'library of pairs', such as a Fab phage display library.

First and second binding sites are relative terms (relative to each other) and are nominal labels given to the binding sites to differentiate one from the other. If one binding site is labeled "the first" then the other is labeled "the second".

First cognate pair and second pair are also relative labels to nominally differentiate the pairs. One pair labeled "first pair" herein is not definitive for the position in the molecule.

Variable domains may have been optimized and/or humanized.

Optimised/humanized variable domains derived from a cognate pair will still be considered a cognate pair after optimization/humanization.

CL as employed herein refers to the constant region portion in the light chain, which may be a naturally occurring light chain constant region.

Constant region fragment as employed herein is intended to refer to the constant region portion located between two variable domains, for example non-cognate variable domains, in the heavy chain. The constant region fragment is characterized in that it is attached to two variable domains in the chain of which it forms part.

Fused as employed herein is intended to refer to a continuous amino acid sequence that is uninterrupted, i.e. linked directly via a peptide bond, for example directly to the sequence of the variable domain or conversely the constant region fragment and not joined by a linker. Inserting a non-natural peptide linker into an amino acid sequence disrupts the sequence and thus a peptide linker containing sequence would not be considered to fuse the relevant portions within the meaning of the present specification. The addition of a natural peptide linker would also be considered interruption of the amino acid sequence, if it cannot be considered to form part of the sequence of one or more of the relevant components, such as a variable domain or constant region fragment.

In one embodiment there is provided a recombinant antibody or a heavy/light chain component thereof comprising:

a heavy chain comprising a constant region fragment,
said constant region fragment located between two variable domains which are not a cognate pair,
the heavy chain further comprising an Fc region with at least one domain selected from CH2, CH3 and combinations thereof,
with the proviso that the heavy chain contains no more than one CH1 domain and only contains two variable domains, and
a light chain comprising a constant region fragment located between two variable domains which are not a cognate pair,
wherein said heavy and light chains are aligned to provide a first binding site formed by a first cognate pair of variable domains and a second binding site formed by a second cognate pair of variable domains.

In one embodiment the antibody or heavy/light chain component thereof according to the present disclosure is multivalent for example bi, tri or tetra-valent. That is to say it has two, three or four binding sites.

In one embodiment the antibody or heavy/light chain component thereof avidly binds the target antigen.

In one embodiment the antibody or heavy/light chain component thereof according to the present disclosure is mono-specific. Monospecific as employed herein is intended to refer to the fact that all the binding sites bind the same target antigen. In one aspect of this embodiment all the binding sites bind the same epitope(s) of said antigen. In an alternative embodiment at least two binding sites bind different epitopes on the target antigen.

In one embodiment an antibody or heavy/light single chain component according to the present disclosure is bispecific such that two binding sites specifically bind different or distinct antigens. In one example the first cognate pair bind a first antigen and the second cognate pair bind a second antigen.

Specifically binds as employed herein is intended to refer to antibodies have high affinity for a target antigen (to which it is specific) and which binds antigens to which it is not specific with a low or much lower affinity (or not at all). Methods of measuring affinity are known to those skilled in the art and include such assays as BIAcore.

In one embodiment the "natural" disulfide bond is present between CH1 and CL. The CL domain is derived from either Kappa or Lambda. The natural position for a bond forming cysteine in human cKappa and cLambda is at position 214 (Kabat numbering 4$^{th}$ edition 1987 in Sequences of Proteins of Immunological Interest, US Department of Health and Human Services, NIH, USA). The sequence of cKappa is provided in SEQ ID NO:81 (FIG. 6).

The exact location of the bond forming in cysteine in CH1 depends on the particular domain actually employed. Thus, for example in human gamma-1 the natural position of the disulfide bond is located position 233 (Kabat numbering 4th edition 1987). The position of the bond forming cysteine for other human isotypes such as gamma 2, 3, 4, IgM and IgE is position 127 and for human isotypes IgD and IgA2B it is position 128.

In one embodiment the antibody or heavy/light chain component thereof according to the disclosure has a disulfide bond in a position equivalent or corresponding to that in the naturally occurring CH and CL.

In one embodiment the constant region fragment comprising CH or CL has a disulfide bond which is in a non-naturally occurring position. This may be engineered into the molecule by introducing cysteine(s) into the amino acid chain at the positions required. This non-natural disulfide bond is in addition to or as an alternative to the natural disulfide bond present between CH and CL.

In one embodiment no disulfide bond between CH and CL is present, for example one or more of the natural interchain cysteines have been replaced by another amino acid, such as serine.

In one embodiment each constant region fragment is fused to one variable domain. In one example the heavy chain constant region fragment is fused to one VH domain and the light chain constant region fragment is fused to one VL domain.

In one example the heavy chain constant region fragment is fused to the VH domain of the first cognate pair and the light chain constant region fragment is fused to the VL domain of the first cognate pair.

In one embodiment each constant region fragment is also linked via a peptide, for example an artificial/non-naturally occurring linker such as sequence in Table 2, to a variable domain, for example which is a non-cognate pair to the variable domain fused thereto.

In one example the heavy chain constant region fragment is linked via a peptide to the VH domain of the second cognate pair and the light chain constant region fragment is linked via a peptide to the VL domain of the second cognate pair.

In one embodiment the variable domains which form a binding site, (for example of a cognate pair) are not linked by a disulfide bond. In one embodiment there are no disulfide bonds between the variable domains of any variable domains pairs which form binding sites (for example no disulfide bonds between cognate pairs).

In one embodiment the variable domains of at least one variable domain pair such as cognate pair are linked by a disulfide bond. Typically those variable domain pairs will be linked by a disulfide bond between two engineered cysteines, one in VH and one in VL.

Suitable positions for introducing engineered cysteines are known in the art, some of which are listed below. It will be appreciated that other suitable positions may exist.

In one embodiment the disulfide bond is between (unless the context indicates otherwise Kabat numbering is employed in the list below):

VH37+VL95C see for example Protein Science 6, 781-788 Zhu et al (1997);

VH44+VL100 see for example; Biochemistry 33 5451-5459 Reiter et al (1994); or Journal of Biological Chemistry Vol. 269 No. 28 pp. 18327-18331 Reiter et al (1994); or Protein Engineering, vol. 10 no. 12 pp. 1453-1459 Rajagopal et al (1997);

VH44+VL105 see for example J Biochem. 118, 825-831 Luo et al (1995);

VH45+VL87 see for example Protein Science 6, 781-788 Zhu et al (1997);

VH55+VL101 see for example FEBS Letters 377 135-139 Young et al (1995);

VH100+VL50 see for example Biochemistry 29 1362-1367 Glockshuber et al (1990);

VH100b+VL49;

VH98+VL 46 see for example Protein Science 6, 781-788 Zhu et al (1997);

VH101+VL 46 or

VH105+VL43 see for example; Proc. Natl. Acad. Sci. USA Vol. 90 pp. 7538-7542 Brinkmann et al (1993); or Proteins 19, 35-47 Jung et al (1994).

VH106+VL57 see for example FEBS Letters 377 135-139 Young et al (1995)

The amino acid pairs listed above are in the positions conducive to replacement by cysteines such that disulfide bonds can be formed. Cysteines can be engineered into these positions by known techniques.

Accordingly in one embodiment a variable domain pair of the present invention is linked by a disulphide bond between two engineered cysteine residues, one in VH and one in VL, wherein the position of the pair of engineered cysteine residues is selected from the group consisting of VH37 and VL95, VH44 and VL100, VH44 and VL105, VH45 and VL87, VH100 and VL50, VH100b and VL49, VH98 and VL46, VH101 and VL46, VH105 and VL43 and VH106 and VL57.

In one embodiment a variable domain pair of the present invention is linked by a disulphide bond between two engineered cysteine residues, one in VH and one in VL, which are outside of the CDRs wherein the position of the pair of engineered cysteine residues is selected from the group consisting of VH37 and VL95, VH44 and VL100, VH44 and VL105, VH45 and VL87, VH100 and VL50, VH98 and VL46, VH105 and VL43 and VH106 and VL57.

In one embodiment a variable domain pair of the present invention is linked by a disulphide bond between two engineered cysteine residues wherein the engineered cysteine residue of VH is at position 44 and the engineered cysteine residue of VL is at position 100.

In one embodiment there is a disulfide bond between the variable domains which form a first binding site, for example in the first cognate pair.

In one embodiment there is a disulfide bond between the variable domains which form a second binding site, for example in the second cognate pair.

In one embodiment there is a disulfide bond between the variable domains which form a first binding site and a further disulfide bond between the variable domains which form a second binding site. It will be appreciated that the locations of the cysteine pairs in each of the cognate pairs may be the same or different.

In one or more embodiments herein there are no interchain disulfide bonds in the Fc regions, for example the hinge region thereof.

Alternatively one or more embodiments herein may be provided with one or more (such as two) disulfide bonds in the Fc regions, such as the hinge region thereof.

In one embodiment there is a disulfide bond between the variable domains pair which form a first binding site and/or the variable domains which form a second binding site and one or more disulfide bonds between the Fc regions, such as the hinge region thereof.

In one embodiment there is a disulfide bond between the variable domains in the first cognate pair and/or the variable domains in the second cognate pair and a disulfide bond between the constant region fragments, such as CH and CL. The latter may optionally include one or more disulfide bonds between the Fc regions, such as the hinge region thereof.

A disulfide bond(s) in the Fc region may be in an area approximately corresponding to the hinge region in natural antibodies.

Modified Fc regions may be employed, for example as disclosed in WO2008/131242.

In one embodiment the constant region fragment, for example in the heavy chain, comprises a CH1 domain. In one embodiment the constant region fragment consists of a CH1 domain. In one embodiment a modified CH1 domain is used which terminates at the interchain cysteine, for example at position 233 (Kabat numbering $4^{th}$ edition 1987) of IgG1. The sequence of a modified IgG1 CH1 which terminates at the interchain cysteine is provided in FIG. 5 (SEQ ID NO: 70).

In one embodiment the constant region fragment, for example in the light chain, comprises a CL domain. In one embodiment the constant region fragment in the light chain consists of a CL domain. In one embodiment the constant region fragment in the light chain consists of cKappa or cLambda.

In one embodiment the light chain comprises a CL domain. In one embodiment the constant region in the light chain consists of CL domain, for example cKappa (SEQ ID NO:81).

Accordingly in one embodiment there is provided a recombinant antibody or a heavy/light chain component thereof comprising:
 a heavy chain comprising a constant region fragment consisting of CH1,
 said constant region fragment located between two variable domains which are not a cognate pair,
 the heavy chain further comprising an Fc region with at least one domain selected from CH2, CH3 and combinations thereof,
 with the proviso that the heavy chain only contains one CH1 and only contains two variable domains, and
 a light chain comprising a constant region fragment consisting of a CL domain located between two variable domains which are not a cognate pair,
wherein said heavy and light chains are aligned to provide a first binding site formed by a first cognate pair of variable domains and a second binding site formed by a second cognate pair of variable domains.

In one embodiment the Fc region comprises CH2 and/or CH3 domains. In one embodiment the Fc fragment from the N-terminal is —CH2CH3 see for example CH2CH3 of IgG1 as shown in FIG. 9 (SEQ ID NO: 87). In an alternative embodiment the Fc region comprises or consists of from the N terminal —CH2CH3CH2CH3. The latter may be provided with a linker between the middle CH3 and CH2 (such as —CH2CH3linkerCH2CH3) to allow the terminal CH2CH3 flexibility to align with the first CH2CH3 (which is attached to the C terminal of the remainder of the molecule). See for example WO2008/012543. This Fc arrangement may prolong half-life and/or allow flexibility to control/provide antibody fragments which are not cross-linking, if desired.

In one embodiment from the N-terminal the heavy chain is arranged as follows: a variable domain (for example from first cognate pair) a CH1, a variable domain (for example from second cognate pair) CH2 and CH3. In this arrangement CH1 may, for example be fused to the variable domain from, for example the first cognate pair and linked via a peptide to the variable domain of, for example the second cognate pair. In one example the N-terminus of CH1 is fused to the C-terminus of a variable domain of the first cognate pair and the C-terminus of CH1 is linked via a peptide to the N-terminus of a variable domain of the second cognate pair.

In one embodiment from the N-terminal the heavy chain is arranged as follows: a VH (for example from a first cognate pair) a CH1, a VH (for example from a second cognate pair) CH2 and CH3, for example in this arrangement CH1 may be fused to a VH from, for example the first cognate pair and linked via a peptide to the VH of, for example the second cognate pair.

In one embodiment from the N-terminal the heavy chain is arranged as follows: a VL (for example from a first cognate pair) a CH1, a VL for example from a second cognate pair) CH2 and CH3, for example in this arrangement CH1 may be fused to a VL from, for example the first cognate pair and linked via a peptide to the VL of, for example the second cognate pair.

In one embodiment from the N-terminal the heavy chain is arranged as follows: a VH (from a first cognate pair) a CH1, a VL (from second cognate pair) CH2 and CH3, for example in this arrangement CH1 may be fused to the V1-1 from the first cognate pair and linked via a peptide to the VL of for example the second cognate pair.

In one embodiment from the N-terminal the heavy chain is arranged as follows: a VL (for example from a first cognate pair) a CH1, a VH (for example from a second cognate pair) CH2 and CH3, for example in this arrangement the CH1 may be fused to the VL from, for example the first cognate pair and linked via a peptide to the VH of, for example the second cognate pair.

In one embodiment from the N-terminal the light chain is arranged as follows a VL (for example from a first cognate pair) a CL, a VL (for example from a second cognate pair), for example a CL may be fused to the VL of, for example the first cognate pair and linked via a peptide to the VL of for example the second cognate pair.

In one example the N-terminus of the CL domain is fused to the C-terminus of a variable domain of the first cognate pair and the C-terminus of the CL domain is linked via a peptide to the N-terminus of a variable domain of the second cognate pair.

In one embodiment from the N-terminal the light chain is arranged as follows a VL (for example from a first cognate pair) a CL, a VH (for example from a second cognate pair), for example CL may be fused to the VL of, for example the first cognate pair and linked via a peptide to VH of, for example the second cognate pair.

In one embodiment from the N-terminal the light chain is arranged as follows a VH (for example from first cognate pair) a CL, a VL (for example from second cognate pair), for example a CL may be fused to the VH of, for example the first cognate pair and linked via a peptide to the VL of, for example the second cognate pair.

In one alternative arrangement CL in the light chain is replaced by CH1 and the heavy chain is provided with a CL, for example replacing a CH1 domain therein.

The heavy and light chains will be chosen to form the required binding domains.

In one embodiment the single heavy/light chain components are joined to each other to provide an antibody by a disulfide bond, for example in the hinge region of the heavy chains. Modified hinges may be employed as per Table 1.

A number of modified hinge regions have already been described for example, in U.S. Pat. Nos. 5,677,425, 6,642, 356, WO9915549, WO2005003170, WO2005003169, WO2005003170, WO9825971 and WO2005003171 and these are incorporated herein by reference. The hinge will usually be located between the second variable domain in the heavy chain and the Fc region (CH2CH3). Particular examples of hinges include those shown in Table 1.

TABLE 1

Hinge linker sequences

| SEQ ID NO: | SEQUENCE |
| --- | --- |
| 1 | DKTHTCAA |
| 2 | DKTHTCPPCPA |
| 3 | DKTHTCPPCPATCPPCPA |
| 4 | DKTHTCPPCPATCPPCPATCPPCPA |
| 5 | DKTHTCPPCPAGKPTLYNSLVMSDTAGTCY |
| 6 | DKTHTCPPCPAGKPTHVNVSVVMAEVDGTCY |
| 7 | DKTHTCCVECPPCPA |
| 8 | DKTHTCPRCPEPKSCDTPPPCPRCPA |
| 9 | DKTHTCPSCPA |

In one example the Fc region further comprises a hinge region consisting of the sequence given in any one of SEQ ID NOs 1-9. In one example the Fc region has the sequence given in FIG. 5 (SEQ ID NO:76).

The arrangement of CL in the light chain and CH1 in the constant region fragment in the heavy chain is thought to minimize inappropriate dimerisation.

The inventors believe that by providing variable domains as cognate pairs in the final construct this optimises and maintains the antigen binding properties of the binding site formed by the relevant pair.

The disulfide bridges in the cognate pairs are believed to be advantageous in that they assist in stabilizing the format.

Examples of suitable peptide linkers are given below, for example in Table 2.

TABLE 2

Flexible linker sequences

| SEQ ID NO: | SEQUENCE |
| --- | --- |
| 10 | SGGGGSE |
| 11 | DKTHTS |
| 12 | (S)GGGGS |
| 13 | (S)GGGGSGGGGS |
| 14 | (S)GGGGSGGGGSGGGGS |
| 15 | (S)GGGGSGGGGSGGGGSGGGGS |
| 16 | (S)GGGGSGGGGSGGGGSGGGGSGGGGS |
| 17 | AAAGSG-GASAS |
| 18 | AAAGSG-XGGGS-GASAS |
| 19 | AAAGSG-XGGGSXGGGS-GASAS |
| 20 | AAAGSG- XGGGSXGGGSXGGGS-GASAS |
| 21 | AAAGSG- XGGGSXGGGSXGGGSXGGGS-GASAS |
| 22 | AAAGSG-XS-GASAS |
| 23 | PGGNRGTTTTRRPATTTGSSPGPTQSHY |
| 24 | ATTTGSSPGPT |
| 25 | ATTTGS |
| - | GS |
| 26 | EPSGPISTINSPPSKESHKSP |
| 27 | GTVAAPSVFIFPPSD |
| 28 | GGGGIAPSMVGGGGS |
| 29 | GGGGKVEGAGGGGGS |
| 30 | GGGGSMKSHDGGGGS |
| 31 | GGGGNLITIVGGGGS |
| 32 | GGGGVVPSLPGGGGS |
| 33 | GGEKSIPGGGGS |
| 34 | RPLSYRPPFPFGFPSVRP |
| 35 | YPRSIYIRRRHPSPSLTT |
| 36 | TPSHLSHILPSFGLPTFN |
| 37 | RPVSPFTFPRLSNSWLPA |
| 38 | SPAAHFPRSIPRPGPIRT |
| 39 | APGPSAPSHRSLPSRAFG |
| 40 | PRNSIHFLHPLLVAPLGA |
| 41 | MPSLSGVLQVRYLSPPDL |

TABLE 2-continued

Flexible linker sequences

| SEQ ID NO: | SEQUENCE |
|---|---|
| 42 | SPQYPSPLTLTLPPHPSL |
| 43 | NPSLNPPSYLHRAPSRIS |
| 44 | LPWRTSLLPSLPLRRRP |
| 45 | PPLFAKGPVGLLSRSFPP |
| 46 | VPPAPVVSLRSAHARPPY |
| 47 | LRPTPPRVRSYTCCPTP- |
| 48 | PNVAHVLPLLTVPWDNLR |
| 49 | CNPLLPLCARSPAVRTFP |

(S) is optional in sequences 13 to 16.

Examples of rigid linkers include the peptide sequences GAPAPAAPAPA (SEQ ID NO:64), PPPP (SEQ ID NO:65) and PPP.

In one embodiment the peptide linker is an albumin binding peptide.

Examples of albumin binding peptides are provided in WO 2007/106120 and include:

TABLE 3

| SEQ ID NO: | SEQUENCE |
|---|---|
| 50 | DLCLRDWGCLW |
| 51 | DICLPRWGCLW |
| 52 | MEDICLPRWGCLWGD |
| 53 | QRLMEDICLPRWGCLWEDDE |
| 54 | QGLIGDICLPRWGCLWGRSV |
| 55 | QGLIGDICLPRWGCLWGRSVK |
| 56 | EDICLPRWGCLWEDD |
| 57 | RLMEDICLPRWGCLWEDD |
| 58 | MEDICLPRWGCLWEDD |
| 59 | MEDICLPRWGCLWED |
| 60 | RLMEDICLARWGCLWEDD |
| 61 | EVRSFCTRWPAEKSCKPLRG |
| 62 | RAPESFVCYWETICFERSEQ |
| 63 | EMCYFPGICWM |

Typically these peptide linkers are used to connect the C-terminus of CH1 to the N-terminus of the variable domain of the second cognate pair (typically VH) and the C-terminus of CL to the N-terminus of the variable domain of the second cognate pair (typically VL). Accordingly the peptide linker may be any one of the linkers provided in SEQ ID NOs 10-65 or PPPP or GS. In one example the linker may be any one of the linkers provided in SEQ ID NOs 13-16 but lacking the N-terminal serine (S). Preferably the peptide linker is SGGGGSGGGGS (SEQ ID NO:72).

It will be appreciated that one or more amino acid substitutions, additions and/or deletions may be made to the antibody variable domains, provided by the present invention, without significantly altering the ability of the antibody to bind to target antigen and to neutralise activity thereof. The effect of any amino acid substitutions, additions and/or deletions can be readily tested by one skilled in the art, for example by using the in vitro assays, for example a BIAcore assay.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody Fc domain chain given in FIGS. 5 and 9 SEQ ID NOs: 76 and 87 may be absent.

In one embodiment the antibody heavy chain comprises a CH1 domain and the antibody light chain comprises a CL domain, either kappa or lambda.

The antibody molecules of the present invention suitably have a high binding affinity for each antigen, in particular picomolar. Affinity may be measured using any suitable method known in the art, including BIAcore. In one embodiment the antibody molecule of the present invention has a binding affinity of about 100 pM or better. In one embodiment the antibody molecule of the present invention has a binding affinity of about 50 pM or better. In one embodiment the antibody molecule of the present invention has a binding affinity of about 40 pM or better. In one embodiment the antibody molecule of the present invention has a binding affinity of about 30 pM or better. In one embodiment the antibody molecule of the present invention is fully human or humanised and has a binding affinity of about 100 pM or better.

The antibody molecules or heavily/light chain components thereof of the present invention may bind one or more antigens of interest and are capable of binding at least two antigens simultaneously.

In one example the first cognate pair of variable domains bind to a first antigen of interest while the second cognate pair of variable domains bind to a second antigen of interest.

In one embodiment, an antigen of interest bound by the antibody molecule or heavy/light chain component thereof may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, CD134 (OX40), ICOS, BCMP7, CD137, CD27L, CDCP1, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, and VEGF, and where appropriate, receptors thereof.

Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment, the antibody molecules of the invention may be used to functionally alter the activity of the antigen of interest. For example, the antibody molecule may neutralize, antagonize or agonise the activity of said antigen, directly or indirectly.

In one embodiment the antigen of interest is human serum albumin (HSA).

In one embodiment the first cognate pair of variable domains bind OX40 and the second pair of variable domains bind human serum albumin. In one example the Heavy chain comprises the sequence given in FIG. 9 (SEQ ID NO:86) and the light chain comprises the sequence given in SEQ ID NO:88).

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, $Lu^{117}$, $Bismuth^{213}$, $Californium^{252}$, $Iridium^{192}$ and $Tungsten^{188}$/$Rhenium^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971). In one example the antibody molecule of the present invention is modified wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

In one embodiment a PEG molecule is linked to a cysteine 171 in the light chain, for example see WO2008/038024 incorporated herein by reference.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

The present invention also provides isolated DNA encoding an antibody described herein or a fragment thereof of a heavy or light chain thereof.

In a further aspect there is provided a vector comprising said DNA.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

In a further aspect there is provided a host cell comprising said vector and/or DNA.

Any suitable host cell/vector system may be used for expression of the DNA sequences encoding the antibody molecule of the present invention. Bacterial, for example *E. coli*, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector (and/or DNA) of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies and fragments according to the present disclosure are expressed at good levels from host cells. Thus the properties of the antibodies and/or fragments are optimised and conducive to commercial processing.

The antibodies of the present invention are useful in the treatment and/or prophylaxis of a pathological condition.

Thus there is provided an antibody or single chain component thereof for use in treatment, for by administering a therapeutically effective amount thereof. In one embodiment the antibody or single chain component thereof is administered in as a pharmaceutical formulation.

Thus the present invention also provides a pharmaceutical or diagnostic composition comprising an antibody molecule of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment the antibody, fragment or composition according to the disclosure is employed in combination with a further pharmaceutically active agent, for example a corticosteroid (such as fluticasonoe propionate) and/or a beta-2-agonist (such as salbutamol, salmeterol or formoterol) or inhibitors of cell growth and proliferation (such as rapamycin, cyclophosphmide, methotrexate) or alternative a CD28 and for CD40 inhibitor. In one embodiment the inhitor is a small molecule. In another embodiment the inhibitor is an antibody specific to the target.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pH of the formulation is 7 then a pI of from 8-9 or above may be appropriate. Whilst not wishing to be bound by theory it is thought that this may ultimately provide a final formulation with improved stability, for example the antibody or fragment remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 ml, of solvent/solution buffer.

The antibodies of the present disclosure are thought to be suitable for delivery via nebulisation.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

The present invention is further described by way of illustration only in the following examples, which refer to the accompanying Figures.

EXAMPLES

Generation of Antibody (FabFv)$_2$Fc

The (FabFv)$_2$Fc (FIG. 3D) was generated by overlapping PCR method that linked an existing A26 gH2 Fab 2G4S 645 gH1 coding region to gamma 1 Fc (See FIGS. 4 and 5). The junction being the end of 645 gH1 and the lower hinge of g1 Fc. The above coding region was cloned into our standard UCB mammalian expression vector under the control of the HCMV-MIE promoter and SV40E polyA. The DNA was paired with a similar plasmid encoding the corresponding light chain (A26 gL8 CK 2G4S 645 gL1, see FIGS. 6 and 7) and used to transfect HEK293 cells in 6-well dishes. Invitrogen's 293fectin was used to transfect the cells and then the cells were incubated for 6 days on a shaking platform at 37° C. Supernatants were harvested and the amount of secreted antibody quantified by ELISA. The supernatants were then submitted for BIAcore analysis. The sequences for the antibody are shown in FIGS. 4-7.

BIAcore Assay

A26Fab is specific for OX40 and 645Fv has specificity for human serum albumin (HSA). 645 has previously been described in WO2009040562.

Binding affinities and kinetic parameters for the interaction of (A26Fab-645Fv)$_2$-Fc (with a format shown in FIG. 3D) with HSA (Jackson ImmunoResearch, 009-000-051) and hOX40 (Ancell 513-020) were determined by surface plasmon resonance (SPR) conducted on a Biacore 3000 using CM5 sensor chips and HBS-EP (10 mM HEPES (pH7.4), 150 mM NaCl, 3 mM EDTA, 0.005% v/v surfactant P20) running buffer. The (A26Fab-645Fv)$_2$-Fc samples were captured to the sensor chip surface using either a human Fc-specific goat F(ab')$_2$ (Jackson ImmunoResearch, 109-006-098) or an in-house generated anti-human CH1 monoclonal antibody. Covalent immobilisation of the capture antibody was achieved by standard amine coupling chemistry.

Each assay cycle consisted of firstly capturing the (A26Fab-645Fv)$_2$-Fc using a 1 min injection, before an association phase consisting of a 3 min injection of antigen, after which dissociation was monitored for 10 min. After each cycle, the capture surface was regenerated with 2×1 min injections of 40 mM HCl followed by 30 s of 5 mM NaOH. The flow rates used were 10 μl/min for capture, 300 min for association and dissociation phases, and 10 μl/min for regeneration.

Titrations of human serum albumin were performed at concentrations of 500, 250, 125 and 62.5 μM. A blank flow-cell was used for reference subtraction and buffer-blank injections were included to subtract instrument noise and drift.

Kinetic parameters were determined by simultaneous global-fitting of the resulting sensorgrams to a standard 1:1 binding model using BiaEvaluation software v3.2.

In order to test for simultaneous binding of antigens to the (A26Fab-645Fv)$_2$-Fc, 3 min injections of either separate 2 μM HSA or 50 nM hOX40, or a mixed solution of 2 μM HSA and 50 nM OX40 were injected over the captured sample.

Results

Kinetic binding analysis by SPR was conducted to assess the interactions of human serum albumin (HSA) to the (A26Fab-645Fv)$_2$-Fc fusion, when captured using either anti-Fc or anti CH1 antibody. The kinetic parameters for HSA binding were not significantly affected by the differing capture method (Table A).

The potential for the (A26Fab-645Fv)$_2$-Fc construct to bind simultaneously to both human serum albumin and human OX40 was assessed by capturing the (A26Fab-645Fv)$_2$-Fc to the sensor chip surface, before performing either separate 3 min injections of 2 μM HSA or 50 nM human OX40, or a mixed solution of both 2 μM HSA and 50 nM OX40. Capture was achieved using either an anti-Fc or anti-CH1 antibody. For each capture method the response seen for the combined HSA/OX40 solution was almost identical to the sum of the responses of the independent injections (Table B). This shows that the (A26Fab-645Fv)$_2$-Fc is capable of simultaneous binding to both HSA and OX40, with the Fc portion of the fusion remaining accessible for binding.

TABLE A

Affinity and kinetic parameters determined for HSA binding to (A26-645Fv)$_2$-Fc captured using anti-Fc or anti-CHI antibody.

| Construct | Capture | ka (x10$^4$M-1s-1) | kd (x10-5s-1) | KD (x10-9M) |
|---|---|---|---|---|
| (A26-645Fv)$_2$-Fc | anti-CH1 | 6.2 | 6.00 | 0.97 |
| (A26-645Fv)$_2$-Fc | anti-Fc | 3.8 | 7.14 | 1.88 |

TABLE B

The binding response (RU) seen after separate injections of HSA or OX40, or injection of premixed HSA and OX40. In each case the final concentration was 2 μM albumin HSA and 50 nM OX40. The capture antibody used is indicated. The sum of the individual HSA and OX40 responses is shown in parentheses.

| Construct | Capture antibody | Analyte | Binding (RU) |
|---|---|---|---|
| (A26Fab-645Fv)$_2$-Fc | Anti-CH1 | HSA | 106.7 |
| | | OX40 | 74.2 |
| | | HSA + OX40 | 179.6 (180.9) |
| (A26Fab-645Fv)$_2$-Fc | anti-Fc | HSA | 65.8 |
| | | OX40 | 54.6 |
| | | HSA + OX40 | 118.4 (120.4) |

Table C and D below provide comparative BIAcore data for different constructs

TABLE C

Summary of HSA binding to A26 Fab-645-Fv and IgG-645-Fv fusions

| Construct | Albumin | ka (1/Ms) | kd (1/s) | KD (nM) | Stoichiometry |
|---|---|---|---|---|---|
| A26-Fab-645-Fv | HSA | 1.68E+04 | 1.16E−04 | 6.92 | 0.71 |
| A26-Fab | HSA | No binding | | | |
| (A26Fab-645Fv)$_2$-Fc | HSA | 6.21E+04 | 6.00E−05 | 0.97 | 0.55 |
| A26-IgG | HSA | No binding | | | |

TABLE D

| Dual HSA and hOX40 binding (HSA at 2 uM, hOX40 at 50 nM) | | | |
|---|---|---|---|
| Construct | Analyte | Buffer corrected Response | OX40 + HSA response |
| A26-Fab | HSA | 5.84 | |
| | hOX40 | 99.02 | |
| | HSA + hOX40 | 103.1 | 104.86 |
| A26-Fab-645-Fv | HSA | 106.65 | |
| | hOX40 | 74.23 | |
| | HSA + hOX40 | 179.55 | 180.88 |
| A26-IgG | HSA | 3.12 | |
| | hOX40 | 97.91 | |
| | HSA + hOX40 | 101.68 | 101.03 |
| (A26Fab-645Fv)$_2$-Fc | HSA | 107.6 | |
| | hOX40 | 79.54 | |
| | HSA + hOX40 | 186.19 | 187.14 |

SDS-Page

To 26 μL of sample was added 10 μL 4× lithium dodecyl sulphate dissociation buffer, and for non-reduced samples 4 μL of 100 mM N-ethyl maleimide, for reduced samples 4 μL of 10× reducing agent. The samples were vortexed, incubated at 100° C. for 3 mins, cooled and centrifuged at 16000×g for 30 secs. 15 μl of the prepared samples were loaded on to 4-20% acrylamine Tris/Glycine SDS gels and run for 100 mins at 125V, constant voltage. The gels were stained with Coomassie Blue protein stain and destained in 7.5% acetic acid.

The results are shown in FIG. 8. FIG. 8 shows a Coomassie Blue stained 4-20% polyacrylamide gel. The samples have all been run under non-reducing (left half of gel) and reducing (right half of gel) conditions. The 4 lanes labelled gA26IgG were mammalian cell supernatants containing expressed full length IgG. Under non-reducing conditions there is one major band at ~200 kDa which is the whole antibody comprising two heavy chains (vH1-CH1-CH2-CH3) and two light chains (vK-CK) linked by disulphide bonds. Under reducing conditions there are 2 major bands, one at ~55 kDa which is the heavy chain and one at ~30 kDa which is the light chain. The 2 lanes labelled gA26Fab-Fv645 were mammalian cell supernatants containing expressed Fab-Fv. Under non-reducing conditions there is one major band at ~100 kDa which is the whole Fab-Fv comprising two chains of approximately equal size, one heavy chain (vH1-CH1-vH2) and one light chain (vK1-CK-vK2) linked by disulphide bonds. Under reducing conditions there is one major band at ~40 kDa which is both the heavy chain (vH1-CH1-vH2) and the light chain (vK1-CK-vK2). The 2 lanes labelled (gA26Fab-Fv645)$_2$-Fc were mammalian cell supernatants containing expressed (Fab-Fv)$_2$-Fc. Under non-reducing conditions there is one major band at >200 kDa which is the whole (Fab-Fv)$_2$-Fc comprising two heavy chains (vH1-CH1-vH2-CH2-CH3) and two light chain (vK1-CK-vK2) linked by disulphide bonds. Under reducing conditions there are two major bands, one is at ~65 kDa which is the heavy chain (vH1-CH1-vH2-CH2-CH3) and one is at ~40 kDa which is the light chain (vK1-CK-vK2). Most other bands are irrelevant supernatant proteins that are equivalent between the samples. The banding pattern observed for the (gA26Fab-Fv645)$_2$-Fc is as expected when compared to the banding pattern observed for the IgG and Fab-Fv controls. All constructs expressed well. The band intensity suggests that the IgG and Fab-Fv were expressed as similar levels, whereas the (Fab-Fv)$_2$-Fc was expressed at a lower level.

The invention claimed is:

1. A recombinant bispecific antibody or a heavy/light chain component, which is a heavy chain and associated light chain, consisting of:
   (a) a heavy chain consisting of, from N to C terminal, VH1 domain-CH1 domain-first flexible linker-VH2 domain-Fc fragment, wherein:
      (i) the first flexible linker has the amino acid sequences set forth in any one of SEQ ID NOs:10-49 or 72;
      (ii) the Fc fragment is CH2CH3 directly linked to the VH2 domain via a hinge region having the amino acid sequence set forth in any one of SEQ ID NOs:1-9;
      (iii) the VH1 domain and the VH2 domain are not a cognate pair; and
      (iv) the heavy chain contains no more than one CH1 domain and only contains two variable domains; and
   (b) a light chain consisting of, from N to C terminal, VL1 domain-CL-second flexible linker-VL2 domain, wherein:
      (i) CL is a Ckappa or Lambda;
      (ii) the second flexible linker has the amino acid sequence set forth in any one of SEQ ID NOs:10-49 or 72; and
      (iii) the VL1 domain and the VL2 domain are not a cognate pair;
   wherein the heavy and light chains are aligned to provide a first binding site formed by a first cognate pair of the VH1 domain and the VL1 domain and a second binding site formed by a second cognate pair of the VH2 domain and the VL2 domain;
   wherein there is a disulfide bond between the VH2 domain and the VL2 domain between two engineered cysteines at positions VH44 and VL100;
   wherein there is a disulfide bond between the CH1 domain and the CL; and
   wherein there is no disulfide bond between the flexible linker in the heavy and light chain.

2. The recombinant antibody or the heavy/light chain component thereof of claim 1, wherein the VH1, the VH2, the VL1, and the VL2 are humanized.

3. The recombinant antibody or the heavy/light chain component thereof of claim 1, wherein the first and/or the second flexible inkers have the amino acid sequence set forth in any one of SEQ ID NOs:12-16.

4. The recombinant antibody or the heavy/light chain component thereof of claim 1, wherein there are no inter-chain disulfide bonds present in the hinge region.

5. The recombinant antibody or the heavy/light chain component thereof of claim 1, wherein at least one inter-chain disulfide bond is present in the hinge region.

6. The recombinant antibody or the heavy/light chain component thereof of claim 1, wherein the second cognate pair of the second variable domain has affinity for human serum albumin.

7. The recombinant antibody or the heavy/light chain component thereof of claim 1, wherein the second cognate pair of the second variable domain comprises three heavy chain complementarity determining regions (CDRs) from a heavy chain variable region set forth in SEQ ID NO:74 and three light chain CDRs from a light chain variable region set forth in SEQ ID NO:83.

8. The recombinant antibody or the heavy/light chain component thereof of claim 7, wherein the second cognate pair of the second variable domain comprises a heavy variable region set forth in SEQ ID NO:74 and a light variable region set forth in SEQ ID NO:83.

9. A recombinant antibody wherein the heavy chain has the amino acid sequence set forth in SEQ ID NO: 86 and the light chain has the amino acid sequence set forth in SEQ ID NO: 88.

\* \* \* \* \*